United States Patent
Ben et al.

(10) Patent No.: US 9,648,869 B2
(45) Date of Patent: *May 16, 2017

(54) SMALL MOLECULE ICE RECRYSTALLIZATION INHIBITORS AND METHODS OF USE THEREOF

(71) Applicant: THE UNIVERSITY OF OTTAWA, Ottawa (CA)

(72) Inventors: Robert Ben, Ottowa (CA); Chantelle J. Capicciotti, Barrie (CA)

(73) Assignee: THE UNIVERSITY OF OTTAWA, Ottawa (CA)

(*) Notice: Subject to any disclaimer, the term of this patent is extended or adjusted under 35 U.S.C. 154(b) by 108 days.

This patent is subject to a terminal disclaimer.

(21) Appl. No.: 14/403,391

(22) PCT Filed: May 24, 2013

(86) PCT No.: PCT/IB2013/001043
§ 371 (c)(1),
(2) Date: Nov. 24, 2014

(87) PCT Pub. No.: WO2013/175299
PCT Pub. Date: Nov. 28, 2013

(65) Prior Publication Data
US 2015/0157010 A1     Jun. 11, 2015

Related U.S. Application Data

(60) Provisional application No. 61/651,405, filed on May 24, 2012.

(51) Int. Cl.
*A01N 1/00* (2006.01)
*A01N 1/02* (2006.01)

(52) U.S. Cl.
CPC .................. *A01N 1/0221* (2013.01)

(58) Field of Classification Search
CPC .................................... A01N 1/0221

USPC ........................................................ 435/1.3
See application file for complete search history.

(56) References Cited

PUBLICATIONS

Balcerzak, A.K., et al, "The Importance of Hydrophobic Moieties in Ice Recrystallization Inhibitors", RSC Adv., (2013), vol. 3, pp. 3232-3236.

Capicciotti, C.J., et al, "Ice Recrystallization Inhibitors: From Biological Antifreezes to Small Molecules", in Recent Developments in the Study of Recrystallization, edited by Peter Wilson, Published on Feb. 6, 2013 under CC by 3.0 license. (http://dx.doi.org/10.5772/54992).

Tam, R. Y. et al, "Solution Confirmation of C-linked Antifreeze Glycoprotein Analogues and Modulation of Ice Recrystallization", J. Am Chem. Soc. (2009) vol. 131, pp. 15745-15753.

Tam, R. Y., et al, "Hydration Index—A Better Parameter for Explaining Small Molecule Hydration in Inhibition of Ice Rcrystallization", J. Am Chem. Soc., (2008) vol. 130, pp. 17494-17501.

Capicciotti, C. J., et al.: "Potent Inhibition of Ice Recrystallization by Low Molecular Weight Carbohydrate-based Surfactants and Hydrogelators", Chem. Sci., May 1, 2012 (May 1, 2012), vol. 3, No. 5, pp. 1408-1416; ISSN 2041-6520.

Gibson, M. I.: "Slowing the Growth of Ice with Synthetic Macromolecules: Beyond Antifreeze(glyco) Proteins", Polym. Chem., Oct. 1, 2010 (Oct. 1, 2010), vol. 1, No. 8, pp. 1141-1152; ISSN 1759-9954.

Deller, R. C., et al.: "Ice Recrystallization Inhibition by Polyols: Comparison of Molecular and Macromolecular Inhibitors and Role of Hydrophobic Units", Biomater. Sci., May 1, 2013 (May 1, 2013), vol. 1, No. 5, pp. 478-485; ISSN 2047-4830.

International Search Report and Written Opinion of the International Searching Authority for PCT/IB2013/001043, mailed Sep. 25, 2013; ISA/CA.

*Primary Examiner* — Kara Johnson
(74) *Attorney, Agent, or Firm* — Harness, Dickey & Pierce, P.L.C.

(57) ABSTRACT

The invention relates to small molecule ice recrystallization inhibitor (IRI) compounds having increased ice recrystallization inhibition activity. The IRI compounds disclosed herein are useful in compositions, kits and methods for cryopreserving biological material such as organs, tissues and cells.

48 Claims, 33 Drawing Sheets

SMALL MOLECULE ICE RECRYSTALLIZATION INHIBITORS AND METHODS OF USE THEREOF

CROSS REFERENCE TO RELATED APPLICATIONS

This application is a U.S. National Phase Application under 35 U.S.C. 371 of International Application No. PCT/IB2013/001043 filed on May 24, 2013. This application is based on and claims the benefit of priority of U.S. Provisional Application No. 61/651,405 filed May 24, 2012. The entire disclosures of all of the above applications are incorporated herein by reference.

FIELD

The present invention relates to compounds with ice recrystallization inhibition activity and methods of cryopreserving biological material using such compounds.

BACKGROUND

Cellular injury resulting from freezing and thawing has been studied for over sixty years. Under slow cooling conditions ice will form outside of the cell, concentrating solutes and creating an osmotic flux. Cells with less permeable membranes will incur increasing osmotic pressure resulting in intracellular ice formation and cell rupture if dehydration of the cell cannot occur. However, rapid dehydration may also be lethal to the cell and cryoprotectants are employed to mitigate cellular damage. Cryoprotectants are cytotoxic, and the mechanism of intracellular ice formation and subsequent cell death are not well understood. While the formation of intracellular ice correlates with cell death, it does not directly kill cells. Rather, the process of ice recrystallization (a form of ice crystal re-modeling that occurs during warming), is believed to be a significant factor contributing to cell death. The importance of ice recrystallization as a mechanism of cellular damage is supported by the fact that (1) freeze-tolerant organisms inhabiting sub-zero environments produce large quantities of recrystallization inhibitors in vivo to ensure survival and (2) ice recrystallization damages cell membranes during cryopreservation.

Stem cell and regenerative therapy using cryopreserved umbilical cord blood is hampered by decreased cell function and viability after thawing. Consequently, improved cryopreservation protocols that increase the yield of viable and functional cells are urgently required. Dimethyl sulfoxide (DMSO) is currently regarded as the "gold standard" for cryopreservation of stem cells and umbilical cord blood. While all cryoprotectants are potentially cytotoxic in vitro, DMSO has exhibited significant cytotoxic effects in the clinical setting. Various biopolymers have been explored as an alternative to DMSO, but fail to provide the high cell viabilities observed with DMSO or glycerol. Similarly, various sugars (mono- and disaccharides) have also been investigated as cryoprotectants. However, the structure of the carbohydrate, the freezing protocol, cell type and reported cell viabilities vary dramatically between studies making it difficult to ascertain the true ability of these compounds to protect cells against cryo-injury. To date, a viable alternative to DMSO, has not yet been identified.

Improved cryopreservation compositions and methods have the potential to revolutionize solid organ transplantation by allowing organs such as livers and kidneys to be successfully preserved and transported more widely.

The mechanism of recrystallization (both with inorganic materials and ice) has been studied and several models have emerged.

Biological antifreezes (BAs) are a very interesting class of molecules comprised of antifreeze proteins (AFPs) and antifreeze glycoproteins (AFGPs) which protect organisms inhabiting sub-zero environments from cryo-injury and death. However, attempts to utilize BAs as cryoprotectants have been met with limited success. This is largely because BAs exhibit thermal hysteresis (TH) activity, meaning they have the ability to selectively depress the freezing point of a solution below that of the melting point. The TH activity associated with these compounds is a result of irreversible binding of BAs to the surface of ice, exacerbating cellular damage at cryopreservation temperatures. This is unfortunate as BAs are also potent inhibitors of ice recrystallization.

During the last decade, the rational design of novel compounds based on BAs has featured prominently in the literature. However, only a few of these molecules have the ability to inhibit ice recrystallization, limiting compounds with potent ice recrystallization inhibition activity to BAs (native AFPs and AFGPs), synthetic analogues of AFGPs and polyvinyl alcohol (PVA). It has been demonstrated that C-linked AFGP analogues 1 and 2, shown below

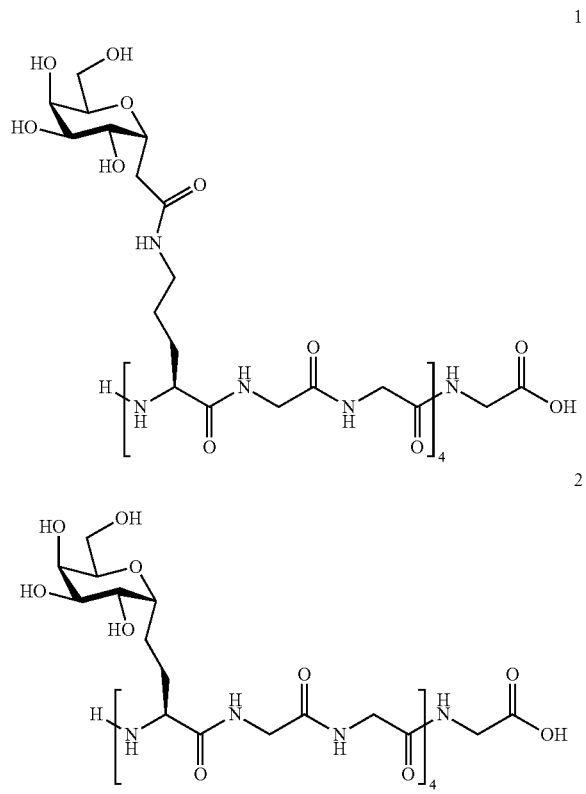

possess "custom-tailored" antifreeze activity. They are potent inhibitors of ice recrystallization but do not exhibit TH activity. The cryoprotective ability of C-linked AFGP analogues 1 and 2 has also been assessed, and analog 1 was found to be as effective as a 2.5% solution of DMSO for the cryopreservation of human embryonic liver cells. It has also been demonstrated that simple mono- and disaccharides are moderate inhibitors of ice recrystallization and that inhibition of ice recrystallization during cryopreservation with human embryonic liver cell lines and human umbilical cord blood leads to increased cell viability after thawing. While these simple carbohydrates classify as small molecules, they are not potent inhibitors of ice recrystallization. Consequently, small molecules exhibiting potent IRI activity are very attractive, but efforts to design such molecules have been impeded because the structural attributes necessary to inhibit ice recrystallization remain unknown.

SUMMARY

To date, there have been no reports of small molecule ice recrystallization inhibitor (IRI) compounds. Without being bound by theory, it is believed that the moderate ice recrystallization inhibition activity observed with simple carbohydrates is based upon their ability to alter the structure of bulk water which is ultimately related to the degree of carbohydrate hydration. Thus, in an effort to identify potent small molecule inhibitors of ice recrystallization, the ability of various small molecules which alter the structure of bulk water and/or sequester bulk water to inhibit ice recrystallization were investigated. Such compounds include surfactants, organogelators and hydrogelators. The ability of representative low molecular weight carbohydrate-based compounds to inhibit ice recrystallization was assessed and it was demonstrated that these compounds are potent IRI compounds.

In one embodiment, compositions for cryopreserving a biological material are provided. The composition comprises at least one IRI compound selected from the group consisting of an alkyl-glycoside, a n-alkyl-aldonamide, a n-alkyl-erythronamide, an aryl-glycoside, an aryl-aldonamide, and a combination thereof; and at least one cryopreservation excipient.

In another embodiment, a kit for cryopreserving a biological material is provided. The kit comprises the compositions for cryopreserving a biological provided herein.

In another embodiment, methods for cryopreserving a biological material are provided. The methods comprise suspending the biological material in a solution comprising at least one IRI compound to form a suspension; and freezing the suspension; wherein the at least one IRI compound is selected from the group consisting of an alkyl-glycoside, a n-alkyl-aldonamide, a n-alkyl-erythronamide, an aryl-glycoside, an aryl-aldonamide, and a combination thereof.

In yet another embodiment, methods of inhibiting ice recrystallization in a biological material are provided. The methods comprise suspending the biological material in a solution comprising at least one ice recrystallization inhibitor (IRI) compound to form a suspension; and cryopreserving the suspension; wherein the at least one IRI compound is selected from the group consisting of an alkyl-glycoside, a n-alkyl-aldonamide, a n-alkyl-erythronamide, an aryl-glycoside, an aryl-aldonamide, and a combination thereof.

Other embodiments, including particular aspects of the embodiments summarized above, will be evident from the detailed description that follows.

BRIEF DESCRIPTION OF THE DRAWINGS

FIG. 4($b$) shows the ice crystal habits of compound 4 assayed at a concentration of 1 mg/mL FIG. 4($c$) shows the ice crystal habits of compound 5 assayed at a concentration of 0.01 mg/mL FIG. 4($d$) shows the ice crystal habits of compound 6 assayed at a concentration of 0.01 mg/mL.

FIG. 4($e$) shows the ice crystal habits of AFGP-8 assayed at a concentration of 0.01 mg/mL in water.

FIG. 5($b$) is a graphical representation of the saturation recovery curves of frozen $D_2O$ with the AFP controls and compound 4 ($R_1=0.0209\pm0.0002$ $s^{-1}$). The concentration at which compound 4 was measured was 44 mM. The concentration compound 4 was corrected to a total overall proton concentration of 1234 mM, unless stated otherwise.

FIG. 5($c$) is a graphical representation of the saturation recovery curves of frozen $D_2O$ with the AFP controls and frozen hydrogel of compound 5 ($R_1=0.0310\pm0.0005$ $s^{-1}$). The concentration at which compound 5 was measured was 42 mM. The concentration of compound 5 was corrected to a total overall proton concentration of 1234 mM, unless stated otherwise.

FIG. 5($d$) is a graphical representation of the saturation recovery curves of frozen $D_2O$ with the AFP controls and frozen hydrogel of compound 6 ($R_1=0.030\pm0.001$ $s^{-1}$). The concentration at which compound 6 was measured was 16 mM, which corresponds to a total overall proton concentration of 479 mM.

DETAILED DESCRIPTION

Figure 1:
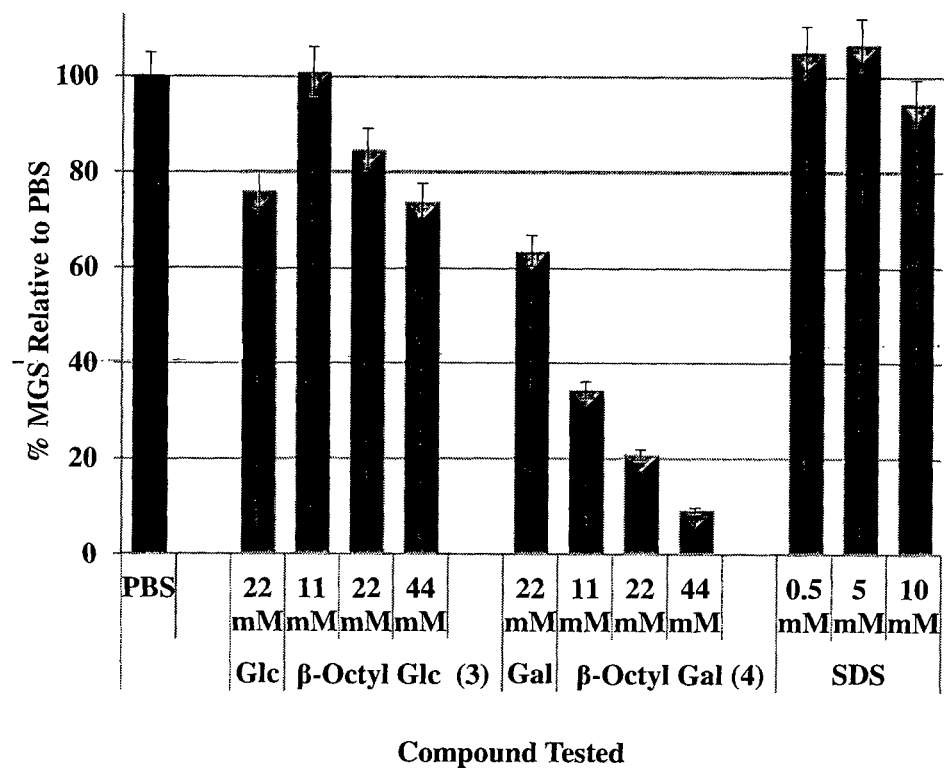
FIG. 1 is a graphical representation of ice recrystallization inhibition activity of compound 3 and compound 4, and anionic surfactant sodium dodecyl sulphate (SDS). All compounds are represented as a % MGS (mean grain size) of ice crystals relative to the phosphate buffered saline (PBS) positive control.

IRI compounds, compositions and kits for cryopreservation, and methods for cryopreserving a biological material are provided herein.

I. Definitions

Unless defined otherwise, all technical and scientific terms used herein have the same meaning as commonly understood by one of ordinary skill in the art to which the invention belongs. In case of conflict, the present application including the definitions will control. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The term "aldonamide" refers to an amide of an aldonic acid, and the term "aldonic acid" refers to a sugar substance in which the aldehyde group (generally found at the C1 position on the sugar) has been replaced by a carboxylic acid. Aldonamides may be based on compounds comprising one saccharide unit, two saccharide units or they may be based on compounds compromising more than two saccharide units as long as the polysaccharide has a terminal sugar unit with an aldehyde group available for oxidation to a carboxylic acid group. Examples of an aldonamide based on one saccharide unit include, but are not limited to, ribonamide, gluconamide, and glucoheptonamide. Examples of an aldonamide based on two saccharide units include, but are not limited to, lactobionamide and maltobionamide. The aldonamide may be substituted or unsubstituted with groups, such as, but not limited to an alkyl group and an aryl group.

The term "alkoxy" refers to straight-chain or branched alkyl group having 1 to about 8 carbons bonded to an oxygen, such as, but not limited to, methoxy, ethoxy, propoxy, butoxy, pentoxy, hexoxy, heptoxy and octoxy. The term "$C_1$-$C_4$-alkoxy" refers to an alkoxy having 1 to 4 carbon atoms such as, but not limited to, methoxy, ethoxy, n-propoxy, 1-methylethoxy, n-butoxy, 1-methylpropoxy, 2-methylpropoxy and 1,1-dimethylethoxy. "Alkoxy" is intended to embrace all structural isomeric forms of an alkoxy group. For example, as used herein, propoxy encompasses both n-propoxy and isopropoxy, etc.

The term "alkyl" refers to a saturated hydrocarbon chain of 1 to about 8 carbon atoms in length, such as, but not limited to, methyl, ethyl, propyl and butyl. The alkyl group may be straight-chain or branched-chain. The term ""$C_1$-$C_4$-alkyl" as used refers to a saturated straight-chain or branched hydrocarbon having 1 to 4 carbon atoms. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl.

The term "aryl" refers to a monocyclic or polycyclic aromatic group, such as, but not limited to, phenyl, napthyl, thienyl and indolyl.

The term "biological material" refers to any substance which can or has to be removed from a human or non-human, such as an animal, body that is suitable for cryopreservation, such as, but not limited to, organs, tissues, cells, sperm, eggs and embryos. Examples of cells include, but are not limited to, a cell line, a stem cell, a progenitor cell, a liver cell and a red blood cell.

The term "carbohydrate" refers to a compound consisting of carbon, hydrogen, and oxygen. Examples include, but are not limited to, monosaccharides, disaccharides, oligosaccharides and polysaccharides as well as substances derived from monosaccharides by reduction of the carbonyl group (alditols), by oxidation of one or more terminal groups to carboxylic acids, or by replacement of one or more hydroxy group(s) by a hydrogen atom, an amino group, a thiol group or similar heteroatomic groups. "Carbohydrate" is intended to encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, substituted, or combinations thereof. Thus, carbohydrate derivatives or substituted carbohydrates include substituted and unsubstituted monosaccharides, disaccharides, oligosaccharides, and polysaccharides.

The term "cell medium" refers to a liquid or gel designed to support the growth of microorganisms or cells, such as, but not limited to, Eagle's Minimum Essential Medium (MEM), Dulbecco's Modified Eagle's Medium (DMEM), Roswell Park Memorial Institute medium (RPMI), Fetal Bovine Serum (FBS), Fetal Calf Serum (FCS), Ham's F-10, Ham's F-12, Hank's buffered salt solution (HBSS), HBSS and dextrose, and Medium 199.

The term "cryopreservation agent" refers to a compound which assists in the cryopreservation of a biological material. Examples of suitable cryopreservation agents include, but are not limited to, DMSO, glycerol, and other biopolymers used in cryopreservation. Examples of suitable biopolymers include, but are not limited to, polyvinyl alcohol. "Cryopreservation agent" as used herein does not include water, RPMI, DMEM, MEM and HBSS and dextrose.

The term "erythronamide" refers to an amide of erythronic acid, and the term "erythronic acid" refers the acid of the carbohydrate, erythrose ($C_4H_8O_4$). An erythronamide substituted with groups such as, but not limited to, an alkyl and a hydroxyalkyl.

The term "halogen" including derivative terms, such as "halo" refers to fluorine, chlorine, bromine and iodine.

The term "haloalkyl" refers to a straight-chain or branched alkyl group substituted with from 1 to the maximum possible number of halogen atoms. The term "$C_1$-$C_4$-haloalkyl" refers to a straight-chain or branched alkyl group having 1 to 4 carbon atoms, where some or all of the hydrogen atoms in the alkyl groups may be replaced by fluorine, chlorine, bromine and/or iodine. Examples of a $C_1$-$C_4$-haloalkyl include, but are not limited to, chloromethyl, dichloromethyl, trichloromethyl, fluoromethyl, difluoromethyl, trifluoromethyl, chlorofluoromethyl, dichlorofluoromethyl and chlorodifluoromethyl.

The term "glycoside" refers to a molecule in which a sugar group is bonded through its anomeric carbon to another group via a glycosidic bond. A "glycosidic bond" may be an O— (an O-glycoside), N— (a glycosylamine), S— (a thioglycoside), or C— (a C-glycoside) bond. The sugar group in a glycoside may be a monosaccharide or an oligosaccharide. The sugar group in a glycoside may be bonded to groups such as, but not limited to, an alkyl group and an aryl group The term "monosaccharide" refers to a simple sugar which upon hydrolysis does not break down into a smaller simple sugar. "Monosaccharide" is intended to encompass an aldose and a ketose. An "aldose" refers to a simple sugar that contains only one aldehyde group per molecule. A "ketose" refers to a simple sugar that contains one ketone group per molecule. Examples of monosaccharides include, but are not limited to, glucose, fructose, galactose, xylose and ribose.

The terms "oligosaccharide" and "polysaccharide" refer to compounds consisting of monosaccharides linked glycosidically. In general polysaccharides comprise at least 10 monosaccharide residues, whereas oligosaccharides in general comprise in the range of 2 to 20 monosaccharides. Oligosaccharides and polysaccharides may be linear or branched.

The term "polyvinyl alcohol (PVA)" refers to water soluble polyhydroxy compounds which can be generally characterized, for instance, by the presence of ($-CH_2-CHOH-$) units in a polymer chain. "Polyvinyl alcohol" includes all suitable grades, degrees of saponification and degrees of polymerization. Examples of polyvinyl alcohols include, but are not limited to, grades of Mowiol®.

The term "pyranose" refers to carbohydrates having a chemical structure that includes a six-membered ring consisting of five carbon atoms and one oxygen atom. For example the sugars including, but not limited to, allose, altrose, glucose, galactose and mannose can be in pyranose form.

The term "sugar" refers to monosaccharides, oligosaccharides, polysaccharides, as well as compounds comprising monosaccharide, oligosaccharide, or polysaccharide. The terms "carbohydrate" and "sugar" are herein used interchangeably.

II. IRI Compounds

In one embodiment, the IRI compound includes a hydrophilic carbohydrate residue linked by an amide bond, ester, or ether group to a hydrophobic structure, which may include an alkyl chain.

In another embodiment, the IRI compound can be derived from a pyranose or open chain carbohydrate as a highly-hydrated group linked at C1 by an amide bond, acetyl or ether group to an alkyl chain or functionalized alkyl chain.

In another embodiment, the IRI compound can include a carbohydrate-based non-ionic surfactant. The carbohydrate-based non-ionic surfactants can include alkyl-glycosides, such as, but not limited to n-octyl-β-D-glycosides. Examples of suitable n-octyl-β-D-glycosides include, but are not limited to, n-octyl-β-D-glucopyranoside (compound 3) and n-octyl-β-D-galactopyranoside (compound 4) below.

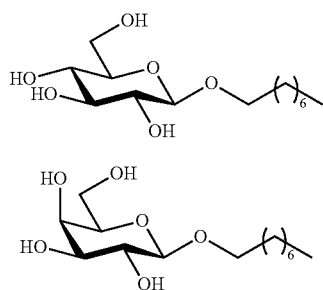

In another embodiment, the IRI compound is a carbohydrate-based hydrogelator. Carbohydrate-based hydrogelators can include n-alkyl-aldonamides such as, but not limited to n-octyl-D-aldonamides. An example of a suitable n-octyl-D-aldonamide is n-octyl-D-gluconamide (compound 5) below.

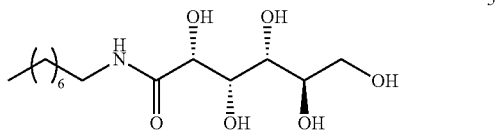

In another embodiment, the IRI compound is a n-alkyl-gluconamide represented by Formula I:

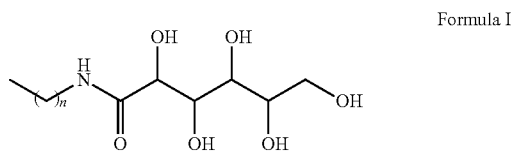

Figure 6:
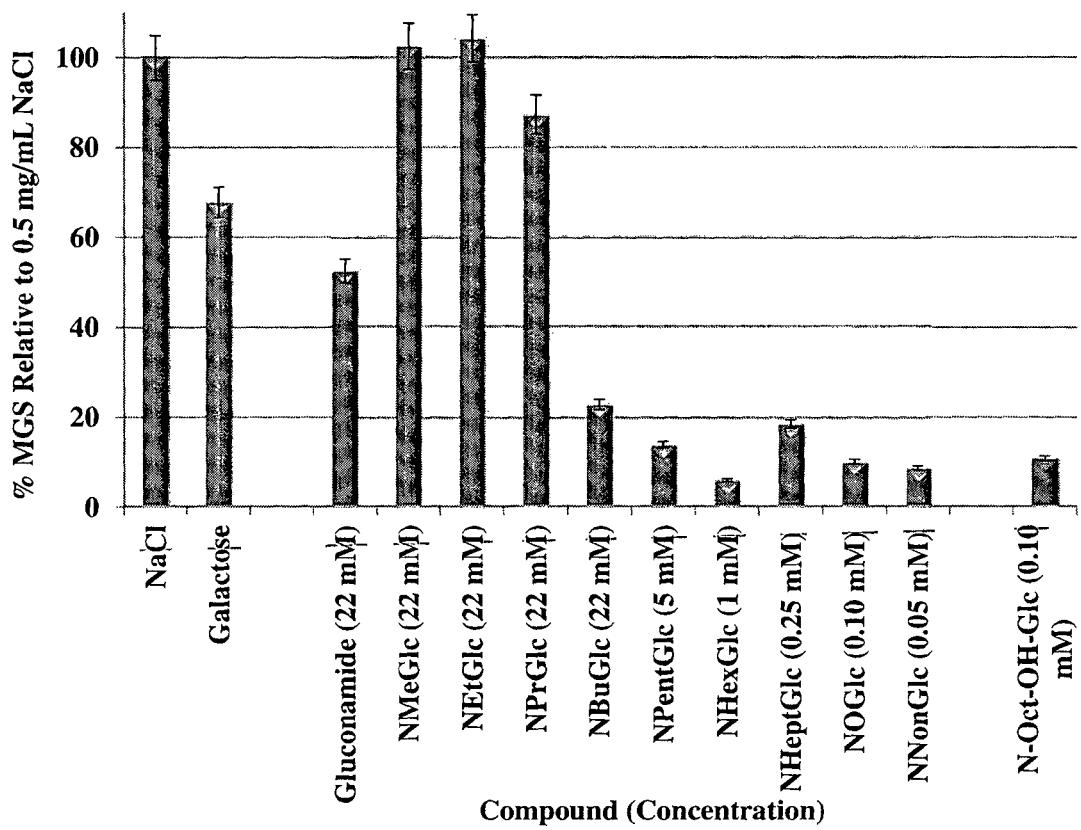
FIG. 6 is a graphical representation of ice recrystallization inhibition activity of n-alkyl-gluconamides in 0.5 gm/mL NaCl.

Formula I wherein n=0, 1, 2, 3, 5, 6, 7, or 8. Non-limiting examples of n-alkyl-gluconamides include n-methyl-gluconamide (NMeGlc), n-ethyl-gluconamide (NEtGlc), n-propyl-gluconamide (NPrGlc), n-butyl-gluconamide (NBuGlc), n-pentyl-gluconamide (NPentGlc), n-hexyl-gluconamide (NHexGlc), n-heptyl-gluconamide (NHepGlc), n-octyl-gluconamide (NOGlc), n-nonyl-gluconamide (NNonGlc), and (N-Oct-OH-GLC). ice recrystallization inhibition activity for the listed n-alkyl-gluconamides is shown in FIG. 6.

In another embodiment, the IRI compound is a n-alkyl-erythronamide or a n-hydroxyalkyl-erythronamide represented by Formula II:

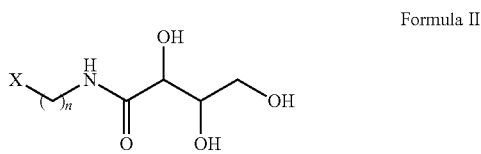

Figure 7:
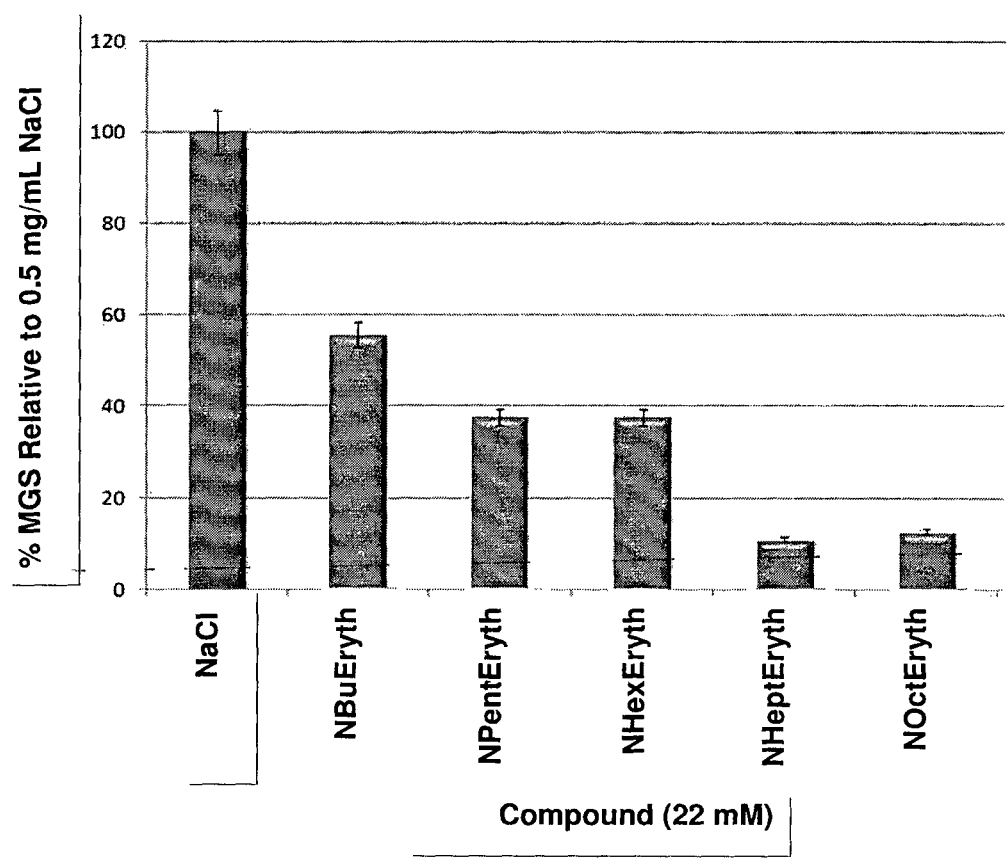
FIG. 7 is a graphical representation of ice recrystallization inhibition activity of n-alkyl-erythronamides in 0.5 gm/mL NaCl.

Formula II wherein X is $-CH_3$ or $-OH$ and n=3, 4, 5, 6, 7, 8. Non-limiting examples of n-alkyl-erythronamides include n-butyl-erythronamide (NBuEryth), n-pentyl-erythronamide (NPentEryth), n-hexyl-erythronamide (NHexEryth), n-heptyl-erythronamide (NHepEryth), and n-octyl-erythronamide (NOEryth). Ice recrystallization inhibition activity for the listed n-alkyl-erythronamides is shown in FIG. 7. Non-limiting examples of a n-hydroxyalkyl-erythronamides include, for example, n-butanol-erythronamide, n-pentenol-erythronamide, n-hexanol-erythronamide, n-heptanol-erythronamide, and n-octanol-erythronamide.

In another embodiment, the IRI compound is a para-, ortho- or meta-substituted aryl-glycoside. Non-limiting examples of para-substituted aryl-glycosides are shown below.

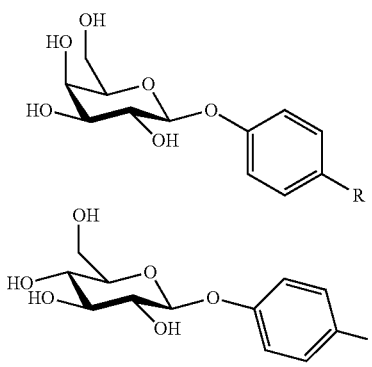

| | | | |
|---|---|---|---|
| 6a: R = Br | 10a: R = CH₃ | 14: R = Br | 18: R = CF₃ |
| 7a: R = Cl | 11: R = H | 15: R = Cl | 19: R = CH₃ |
| 8a: R = F | 12: R = CF₃ | 16: R = F | 20: R = H |
| 9a: R = OCH₃ | 13: R = NO₂ | 17: R = OCH₃ | 21: R = NO₂ |

Figure 8:
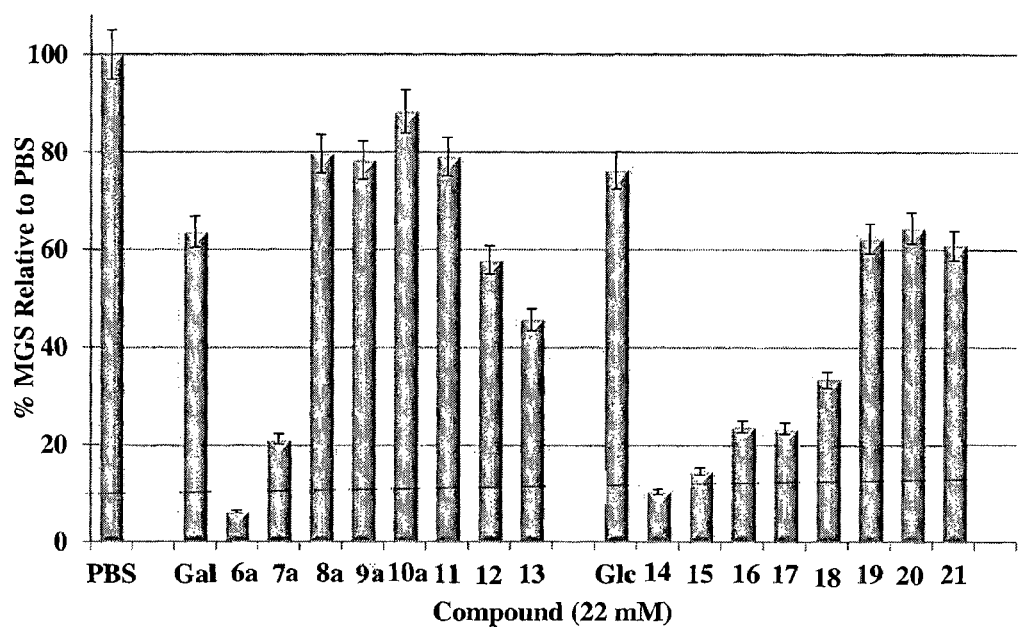
FIG. 8 is a graphical representation of ice recrystallization inhibition activity of para-substituted aryl-glycosides derivatives in PBS.

Ice recrystallization inhibition activity for the para-substituted aryl-glycoside derivatives is shown in FIG. 8. In another embodiment, the para-, ortho- or meta-substituted aryl-glycoside is a para-, ortho- or meta-substituted aryl-glucoside corresponding in structure to Formula A below:

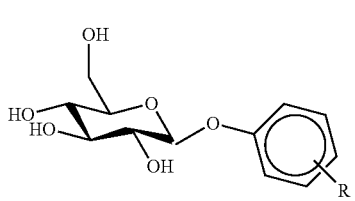

Formula A wherein R is hydrogen, halo, alkoxy, haloalkyl, alkyl or —NO$_2$.

In another embodiment, R is hydrogen; or halo selected from the group consisting of Br, Cl, and F; or $C_1$-$C_4$-alkoxy; or $C_1$-$C_4$-haloalkyl; or $C_1$-$C_4$-alkyl; or —NO$_2$ In another embodiment, R is hydrogen; or halo selected from the group consisting of Br, Cl, and F; or $C_1$-$C_4$-alkoxy.

In another embodiment, R is para-substituted.

In another embodiment, R is halo selected from the group consisting of Br and F; or R is methoxy, wherein R is para-substituted.

Examples of the para-, ortho- or meta-substituted aryl-glucosides corresponding in structure to Formula A are para-methoxy-phenyl glucoside (PMP-Glc) (compound 17), para-fluoro-phenyl glucoside (pFPh-Glc) (compound 16) and para-bromo-phenyl glucoside (PBrPh-Glc) (compound 14).

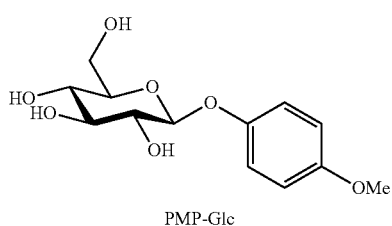

PMP-Glc

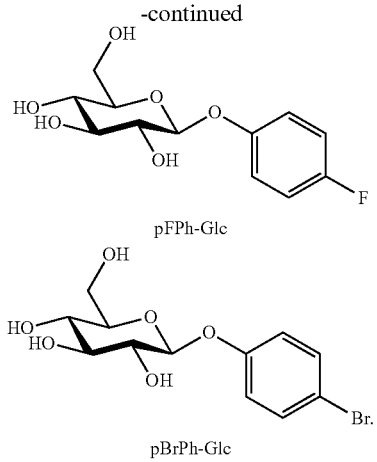

pFPh-Glc pBrPh-Glc

Figure 24:
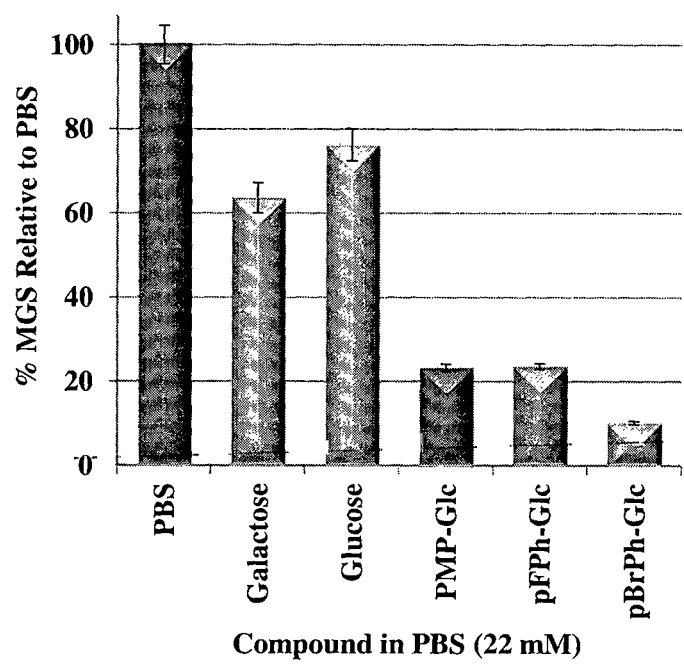
FIG. 24 is a graphical representation of ice recrystallization inhibition activity of aryl-glycosides in PBS, including PMP-Glc, pFPh-Glc and pBrPh-Glc. All compounds are represented as a % MGS (mean grain size) of ice crystals relative to the phosphate buffered saline (PBS) positive control

Ice recrystallization inhibition activity for PMP-Glc, pFPh-Glc and pBrPh-Glc is shown in FIG. 24.

In another embodiment, the IRI compound is an aryl-aldonamide, such as, but not limited to a phenyl-aldonamide. The phenyl-aldonamide can be a compound corresponding in structure to Formula B:

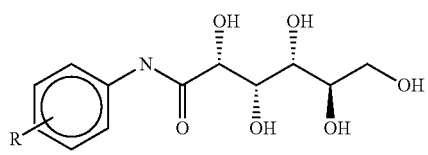

Formula B wherein R is hydrogen; a $C_1$-$C_4$-alkoxy; or halo selected from the group consisting of Br, Cl, and F.

In another embodiment, R is hydrogen; or R is a para-, ortho- or meta-substituted $C_1$-$C_4$-alkoxy; or R is an ortho-substituted halo selected from the group consisting of Br, Cl, and F.

In another embodiment, R is hydrogen; or R is a para-substituted $C_1$-$C_4$-alkoxy; or R is an ortho-substituted halo selected from the group consisting of Br, Cl, and F.

In another embodiment, R is hydrogen; or R is a para-substituted methoxy; or R is an ortho-substituted F.

Examples of compounds corresponding in structure to Formula B are

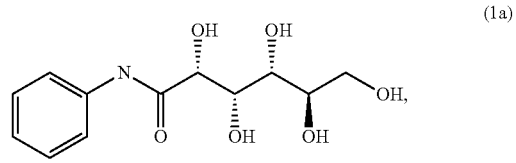

(1a)

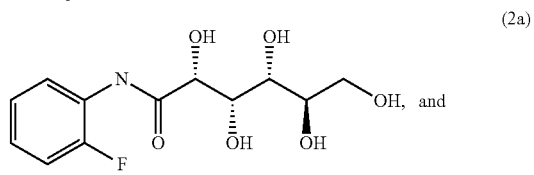

(2a)

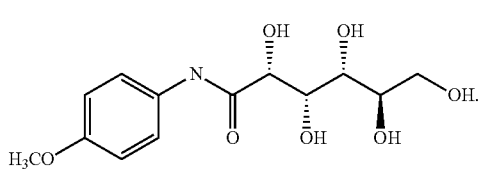
(3a)

In another embodiment, the IRI compound is a carbohydrate with a para-methoxy-phenyl (PMP) substituent at C1 (i.e. a PMP carbohydrate derivative), wherein the carbohydrate is a pyranose or open chain carbohydrate. In further embodiments, the anomeric oxygen may also be replaced with a nitrogen atom.

In a particular embodiment, the IRI compound is a PMP carbohydrate derivative, wherein the carbohydrate is a pyranose, preferably glucose or galactose. An example of a suitable PMP carbohydrate derivative is PMP-glucoside (compound 17/PMP-Glc).

In a further particular embodiment, the MI compound is a PMP carbohydrate derivative, wherein the carbohydrate is a pyranose and the pyranose is linked to a second carbohydrate, preferably galactose, at the C4 position, and preferably where the intersaccharidic linkage is beta-, or equatorial.

In a further embodiment, the IRI compound is a PMP monosaccharide derivative represented by the Formula C below.

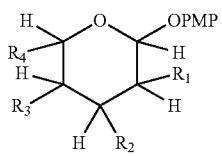

Formula C wherein PMP is

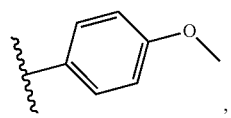 [SMILES: *c1ccc(OC)cc1]

$R_1$-$R_4$ are each independently selected from H,

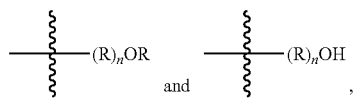

wherein n=0, 1, 2, 3, 4, 5, 6, 7 or 8, and each occurrence of R is independently selected from the group consisting of a $C_1$-$C_9$-alkyl. In some embodiments, at least one of $R_1$, $R_2$, $R_3$ and $R_4$ is OH.

In another embodiment, the IRI compound is a PMP carbohydrate derivative, wherein the PMP substituent in the para-position can be substituted with either bromine, chlorine, fluorine or iodine.

In another embodiment, the IRI compound is a glucose derivative with one or more substituents at the anomeric position. Non-limiting examples of glucose derivatives with a substituent at the anomeric position include:

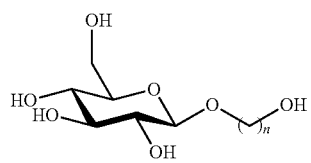

29: n = 2
30: n = 3
31: n = 5
32: n = 6

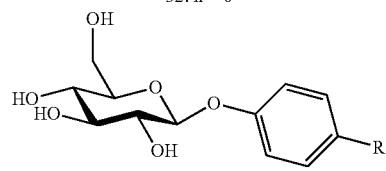

14: R = Br
15: R = Cl
16: R = F
17: R = OCH$_3$
18: R = CF$_3$
19: R = CH$_3$
20: R = H
21: R = NO$_2$

Figure 9:
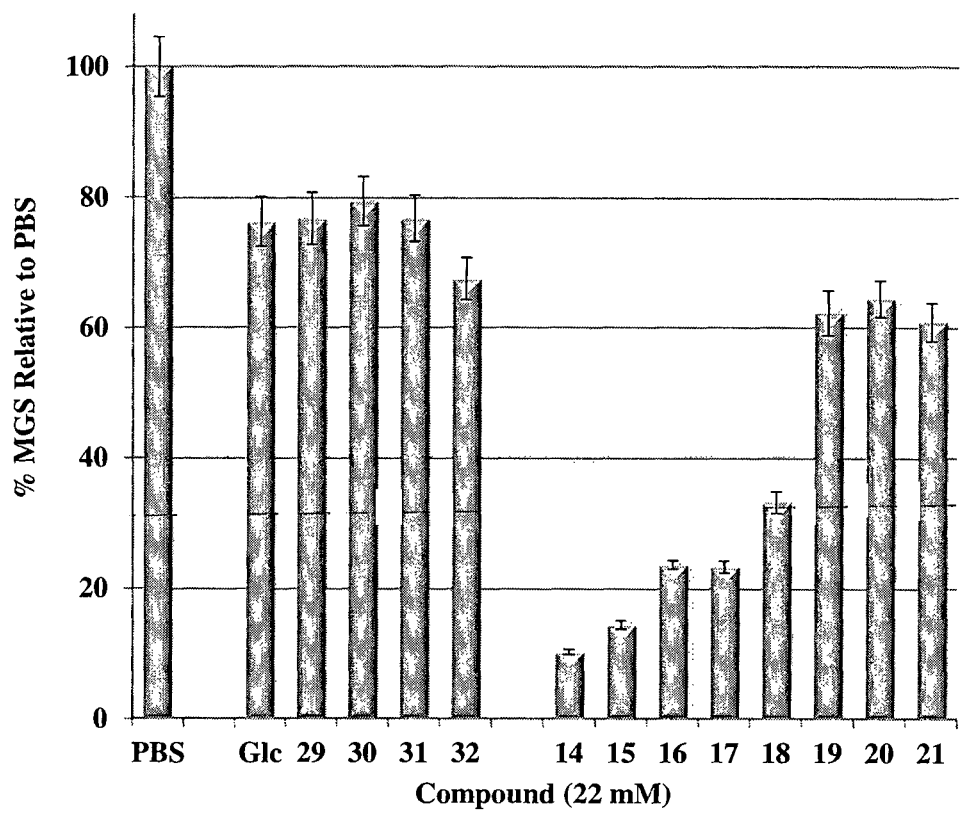
FIG. 9 is a graphical representation of ice recrystallization inhibition activity of glucose derivatives with substituents at the anomeric position in PBS.

Ice recrystallization inhibition activity for the glucose derivatives with substituents at the anomeric position is shown in FIG. 9.

In another embodiment, the IRI compound is an aryl ring substituted with two or more mono- or disaccharides. Non-limiting examples of aryl ring mono- and disaccharides include:

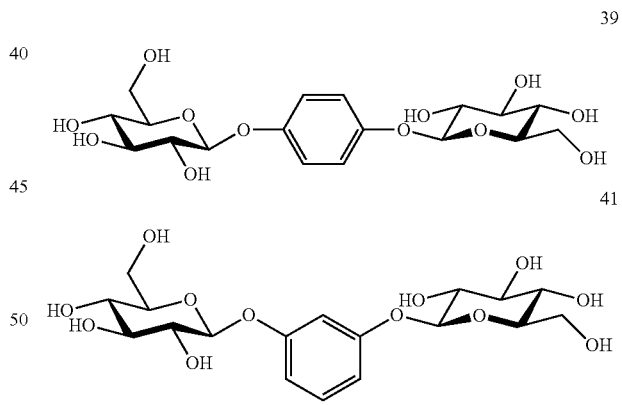

Figure 10:
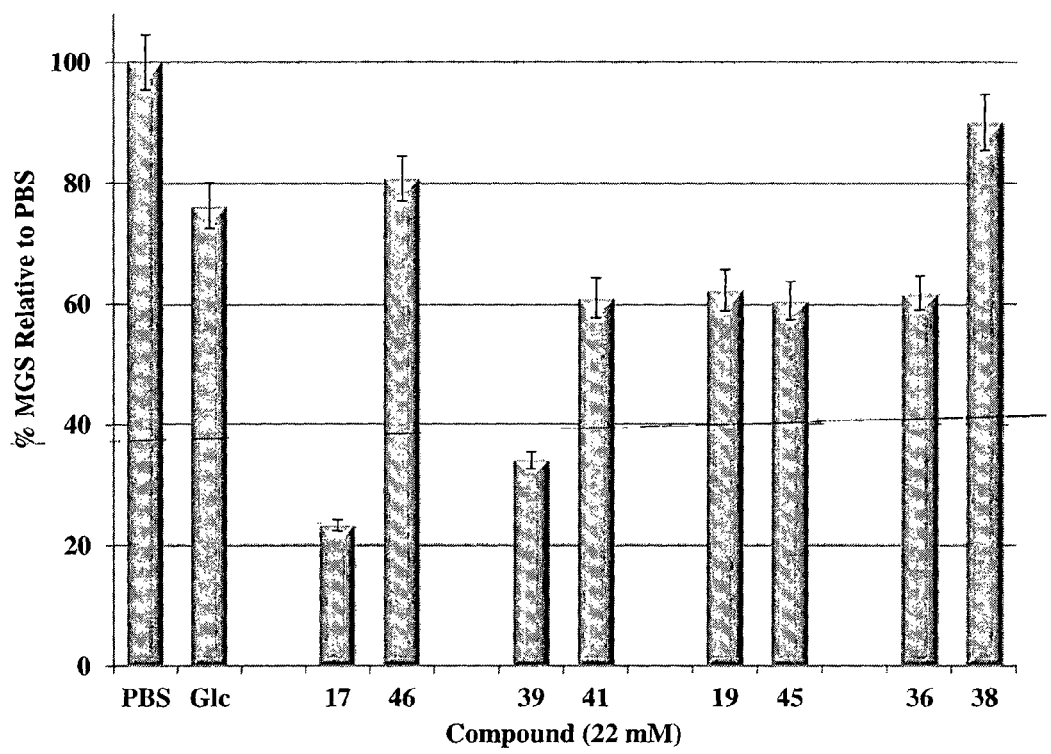
FIG. 10 is a graphical representation of ice recrystallization inhibition activity of aryl mono- and disaccharides in PBS.

Ice recrystallization inhibition activity for the aryl mono- and disaccharides is shown in FIG. 10.

In another embodiment, the IRI compound is a $C_6$—OH modified glycoside derivative. Non-limiting examples of $C_6$—OH modified glycoside derivatives include glucose; xylose; glucuronic acid (compound 1d); 6-deoxy-glucoheptose(compound 2d); 1,6,-anhydro-glucose(compound 3d); galactose; fucose; (2R,3R,4S,5R,6R)-6-ethyltetrahydro-2H-pyran-2,3,4,5-tetraol (compound 4d); (2R,3R,4S,5R,6R)-6-vinyltetrahydro-2H-pyran-2,3,4,5-tetraol (compound 5d); galacturonic acid (compound 6d); 6-deoxy-galacto-heptose (compound 7d); galacto-heptose (compound 8d) and 1,6-anhydro-galactose (compound 9d).

Figure 11:
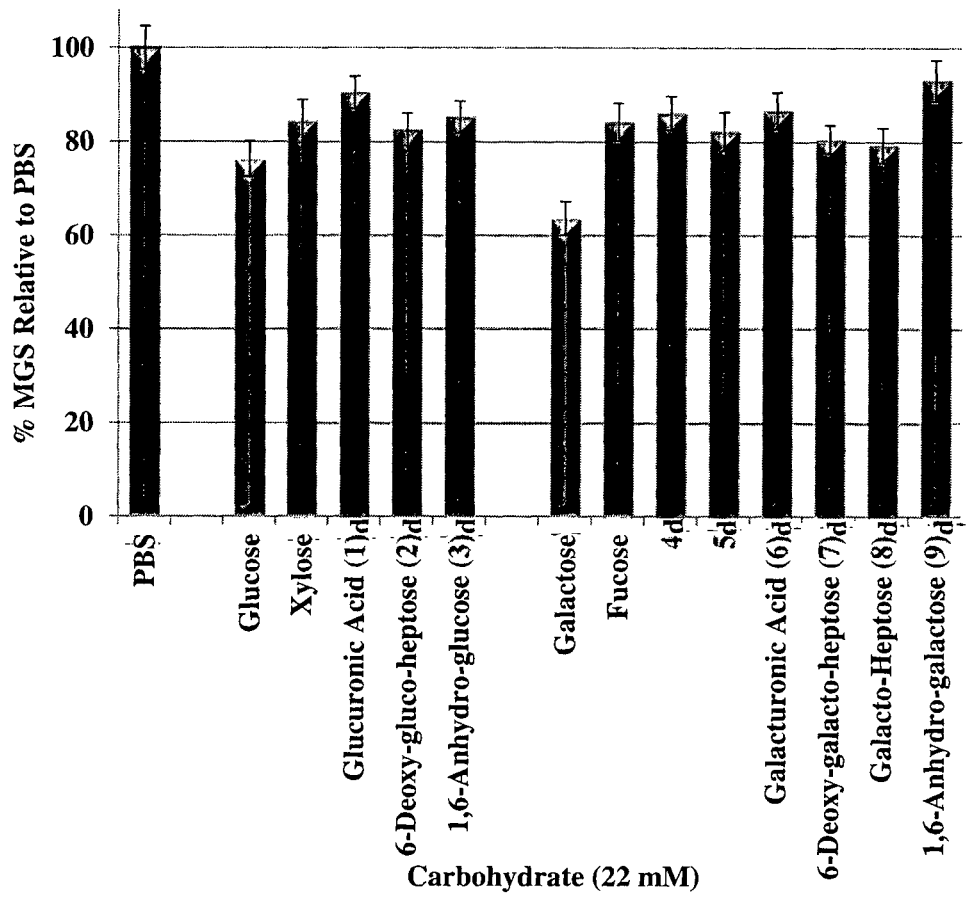
FIG. 11 is a graphical representation of ice recrystallization inhibition activity of $C_6$—OH modified glycoside derivatives in PBS.

Ice recrystallization inhibition activity for the $C_6$—OH modified glycoside derivatives is shown in FIG. 11. In another embodiment, the IRI compound is a disaccharide derivative containing two pyranoses, two open chain carbohydrates, or a pyranose and an open chain carbohydrate, where the two pyranoses, the two open chain carbohydrates or the pyranose and the open chain carbohydrate are linked together with a PMP compound or an alkyl chain.

III. Compositions for Cryopreserving Biological Material

Compositions for cryopreserving a biological material are provided herein comprising at least one IRI compound reported herein and at least one cryopreservation agent reported herein.

In a particular embodiment, compositions for cryopreserving a biological material are provided herein comprising at least one IRI compound, wherein the at least one IRI compound is selected from the group consisting of an alkyl-glycoside, a n-alkyl-aldonamide, a n-alkyl-erythronamide, an aryl-glycoside, an aryl-aldonamide, and a combination thereof.

In a particular embodiment, compositions for cryopreserving a biological material are provided herein, wherein the at least one IRI compound is an aryl-glycoside, an aryl-aldonamide or a combination thereof.

Preferably, the aryl-glycoside is a para-, ortho- or meta-substituted aryl-glycoside, and preferably, the para-, ortho- or mew-substituted aryl-glycoside is a para-, ortho- or meta-substituted aryl-glucoside corresponding in structure to Formula A reported herein. Preferably, the aryl-glucoside corresponding in structure to Formula A is para-substituted. Examples of suitable para-substituted aryl-glucosides for use in the compositions include, but are not limited to, para-methoxy-phenyl glucoside, para-fluoro-phenyl glucoside and para-bromo-phenyl glucoside.

Preferably, the aryl-aldonamide is a phenyl-aldonamide corresponding in structure to Formula B reported herein. Examples of suitable phenyl-aldonamides for use in the composition include, but are not limited to,

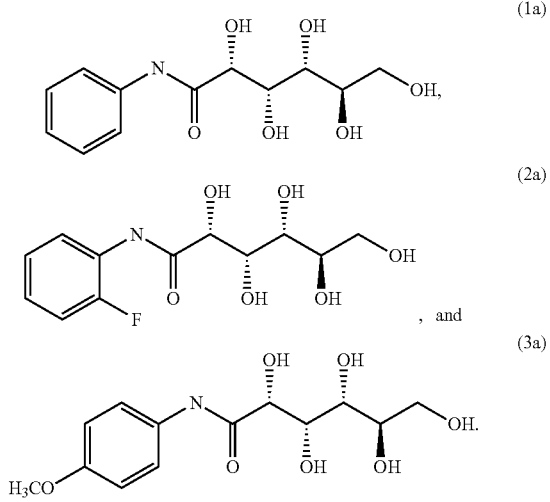

In a particular embodiment, the at least one IRI compound is present in the composition in a concentration of less than about 400 mM, preferably less than about 200 mM, preferably less than about 100 mM, preferably less than about 10 mM, preferably less than about 1 mM, and preferably less than about 0.5 mM. In another embodiment, the IRI compound can be present in the composition in a concentration of about 0.5 mM to (and including) about 400 mM, preferably about 55 mM to (and including) about 220 mM.

In a particular embodiment, the para-, ortho- or meta-substituted aryl-glycoside is present in a concentration between (and including) about 55 mM and about 110 mM.

In a particular embodiment, the aryl-aldonamide is present in the composition in a concentration between (and including) about 30 mM and about 200 mM, and preferably about 55 mM.

In a particular embodiment, compositions for cryopreserving a biological material are provided herein, wherein the at least one cryopreservation agent is selected from the group consisting of DMSO, glycerol, polyvinyl alcohol, other biopolymers, or a combination thereof. The at least one cryopreservation agent is present in the composition in a concentration of about 0.1% to (and including) about 30% w/w, preferably about 0.1% to (and including) about 20% w/w, preferably about 5% to (and including) about 30% w/w, and preferably about 5% to (and including) about 20% w/w.

In a particular embodiment, compositions for cryopreserving a biological material are provided herein which further comprise a biological material. Examples of biological material include, but are not limited to, an organ, a tissue, and a cell. Examples of a cell include, but are not limited to, a cell line, a stem cell, a progenitor cell, a liver cell and a red blood cell, preferably the cell is a red blood cell, a liver cell or a progenitor cell.

In a particular embodiment, compositions for cryopreserving a biological material are provided herein further comprising a cell medium. Examples of suitable cell medium include Eagle's Minimum Essential Medium (MEM), Dulbecco's Modified Eagle's Medium (DMEM), Roswell Park Memorial Institute medium (RPMI), Fetal Bovine Serum (FBS), Fetal Calf Serum (FCS), Ham's F-10, Ham's F-12, Hank's buffered salt solution (HBSS), HBSS and dextrose, and Medium 199 and a combination thereof.

In another embodiment, the compositions for cryopreservation can contain both biological material and cell medium as provided above.

IV. Kits for Cryopreserving Biological Material

Kits for cryopreserving a biological material are provided herein comprising an IRI compound or composition for cryopreserving a biological material as reported herein. The IRI compound and a further cryopreservation agent, if present, may be in the same composition or in separation compositions. Additionally, they may be co-packaged for common presentation or packaged individually. Instructions can also be provided in the kit for cryopreservation of various types of biological material. The kits provided herein can further comprise a cell medium. Examples of suitable cell medium include Eagle's Minimum Essential Medium (MEM), Dulbecco's Modified Eagle's Medium (DMEM), Roswell Park Memorial Institute medium (RPMI), Fetal Bovine Serum (FBS), Fetal Calf Serum (FCS), Ham's F-10, Ham's F-12, Hank's buffered salt solution (HBSS), HBSS and dextrose, and Medium 199 and a combination thereof.

V. Methods for Cryopreserving Biological Material

Methods for cryopreserving a biological material are provided herein by suspending the biological material in a solution of at least one IRI compound reported herein to form a suspension and freezing the suspension.

In a particular embodiment, methods for cryopreserving a biological material are provided herein by suspending the biological material in a solution of at least one IRI compound, wherein the at least one IRI compound is selected from the group consisting of an alkyl-glycoside, a n-alkyl-aldonamide, a n-alkyl-erythronamide, an aryl-glycoside, an aryl-aldonamide, and a combination thereof.

In a particular embodiment, methods for cryopreserving a biological material are provided herein, wherein the at least one IRI compound is an aryl-glycoside, an aryl-aldonamide or a combination thereof.

Preferably, the aryl-glycoside is a para-, ortho- or meta-substituted aryl-glycoside, and preferably, the para-, ortho- or meta-substituted aryl-glycoside is a para-, ortho- or meta-substituted aryl-glucoside corresponding in structure to Formula A reported herein. Preferably, the aryl-glucoside corresponding in structure to Formula A is para-substituted. Examples of suitable para-substituted aryl-glucosides for use in the compositions include, but are not limited to, para-methoxy-phenyl glucoside, para-fluoro-phenyl glucoside and para-bromo-phenyl glucoside.

Preferably, the aryl-aldonamide is a phenyl-aldonamide corresponding in structure to Formula B reported herein. Examples of suitable phenyl-aldonamides for use in the methods include, but are not limited to,

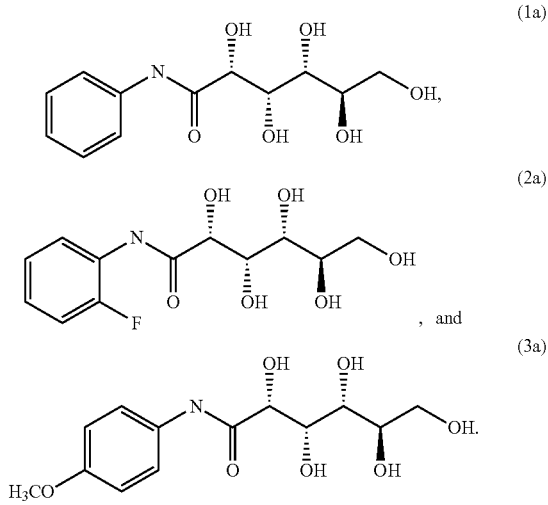

In a particular embodiment, methods for cryopreserving a biological material are provided herein, wherein the at least one IRI compound is present in the solution in a concentration of less than about 400 mM, preferably less than about 200 mM, preferably less than about 100 mM, preferably less than about 10 mM, preferably less than about 1 mM, and preferably less than about 0.5 mM. In another embodiment, the IRI compound can be present in the composition in a concentration of about 0.5 mM to (and including) about 400 mM, preferably about 55 mM to (and including) about 220 mM.

In a particular embodiment, methods for cryopreserving a biological material are provided herein, wherein the IRI compound is an n-octyl-D-aldonamide, which is present in a concentration of about 0.5 mM or less.

In a particular embodiment, methods for cryopreserving a biological material are provided herein, wherein the IRI compound is n-octyl-β-D-galactopyranoside, which is present in a concentration of about 22 mM.

In a particular embodiment, methods for cryopreserving a biological material are provided herein, wherein the IRI compound is a PMP carbohydrate derivative.

In a particular embodiment, methods for cryopreserving a biological material are provided herein, wherein the PMP carbohydrate derivative is present in a concentration of about 110 mM.

In a particular embodiment, methods for cryopreserving a biological material are provided herein, wherein the para-, ortho-, or meta-substituted aryl-glycoside is present in a concentration between (and including) about 55 mM and about 110 mM.

In a particular embodiment, the aryl-aldonomide is present in the composition in a concentration between (and including) about 30 mM and about 200 mM, and preferably about 55 mM.

In a particular embodiment, the biological material is selected from the group consisting of an organ, a tissue, and a cell. Examples of a cell include, but are not limited to, a cell line, a stem cell, a progenitor cell, a liver cell and a red blood cell, preferably the cell is a red blood cell, a liver cell or a progenitor cell.

Methods for cryopreserving a biological material are also provided herein where the biological material is suspended in cell media. Examples of suitable cell media include Eagle's Minimum Essential Medium (MEM), Dulbecco's Modified Eagle's Medium (DMEM), Roswell Park Memorial Institute medium (RPMI), Fetal Bovine Serum (FBS), Fetal Calf Serum (FCS), Ham's F-10, Ham's F-12, Hank's buffered salt solution (HBSS), HBSS and dextrose, Medium 199, and a combination thereof. The method comprises adding the biological material to a solution comprising at least one IRI compound, and then cryopreserving the biological material in cryogenic vials or other suitable container. The vials can be frozen under rate controlled freezing conditions, such as freezing at 1° C. per minute over 16 hours. The vials can be stored using standard cryopreservation techniques, and then they can be thawed when required by removing the vials from the cold storage, and thawing using standard protocols. Examples of standard cryopreservation techniques include freezing in liquid nitrogen to about −196° C. and freezing in dry ice to about −80° C. Examples of standard thawing protocols include ambient thaw or rapid thaw in a water bath between room temperature or 37° C.

In a particular embodiment, methods for cryopreserving a biological material are provided herein by suspending the biological material in a solution of at least one IRI compound and additionally at least one cryopreservation agent, wherein the at least one cryopreservation agent is present in amount equal or less than about 30% w/w, preferably equal or less than about 20% w/w of the total solution. In another embodiment, the at least one cryopreservation agent is present in the composition in a concentration of about 0.1% to (and including) about 30% w/w, preferably about 0.1% to (and including) about 20% w/w, preferably about 5% to (and including) about 30% w/w, and preferably about 5% to (and including) about 20% w/w. Examples of cryopreservation agents include DMSO, glycerol, polyvinyl alcohol, or combinations thereof.

In a particular embodiment, methods for cryopreserving a biological material are provided herein by suspending the biological material in a solution of at least one IRI compound to form a suspension, which is contained in a vial or other suitable container, wherein the vial is frozen directly into the storage unit without a rate controlled freezing protocol.

VI. Methods for Inhibiting Ice Recrystallization in Biological Material Methods for inhibiting ice recrystallization in a biological material are provided herein by suspending suspending the biological material in a solution of at least one IRI compound reported herein to form a suspension and cryopreserving the suspension.

Methods for inhibiting ice recrystallization in a biological material are provided herein, wherein the at least one IRI compound is selected from the group consisting of an alkyl-glycoside, a n-alkyl-aldonamide, a n-alkyl-erythronamide, an aryl-glycoside, an aryl-aldonamide, and a combination thereof.

EXAMPLES

The following examples are merely illustrative, and do not limit this disclosure in any way.

Example 1

Ice Recrystallization Inhibition Activity of Non-Ionic Surfactants n-Octyl-β-D-Glucopyranoside (Compound 3) and n-Octyl-β-D-Galactopyranoside (Compound 4)

n-Octyl-β-D-glycosides are non-ionic surfactants. These surfactants have been studied for many applications including crystallization and solubilisation of membrane proteins as well as lipid-based drug delivery systems. However, one application which has yet to be explored for these surfactants is the ability to inhibit ice recrystallization. Thus, both carbohydrate-based non-ionic surfactants n-octyl-β-D-glucopyranoside (compound 3) and n-octyl-β-D-galactopyranoside (compound 4), were synthesized as detailed in (Capicciotti, C. et al. (2012) "Potent inhibition of ice recrystallization by low molecular weight carbohydrate-based surfactants and Hydrogelators." Chem. Sci. 3:1408-1416) and their ice recrystallization inhibition activity was assessed using a "splat cooling" assay.

In this assay, the area of ice crystals are measured after a 30 minute annealing time at −6.4° C. and compared to a positive control for ice recrystallization resulting in a quantitative measurement of the mean ice grain size. For a positive control, a phosphate buffered saline (PBS) solution was utilized. All samples were normalized to the PBS positive control. The ice recrystallization inhibition activity of the carbohydrate-based non-ionic surfactants n-octyl-β-D-glucopyranoside (compound 3) and n-octyl-β-D-galactopyranoside (compound 4) is shown in FIG. 1. The ice recrystallization inhibition activity of n-octyl-β-D-glucopyranoside (compound 3) at 22 mM was identical to that of D-glucose (Glc), as shown in FIG. 1. This result was consistent with what has previously been reported where the nature of the substituent at the C1 position had little influence on the hydration of the monosaccharide and ice recrystallization inhibition activity. Even at a concentration of 44 mM, the ice recrystallization inhibition activity of n-octyl-β-D-glucopyranoside (compound 3) is still identical to that of the 22 mM D-glucose. Interestingly, the ice recrystallization inhibition activity of its diastereomer, n-octyl-β-D-galactopyranoside (compound 4), at 11, 22 and 44 mM was, in all cases, significantly better than 22 mM D-galactose (Gal).

Example 2

Ice Recrystallization Inhibition Activity of Carbohydrate-Based Hydrogelators

Figure 2:
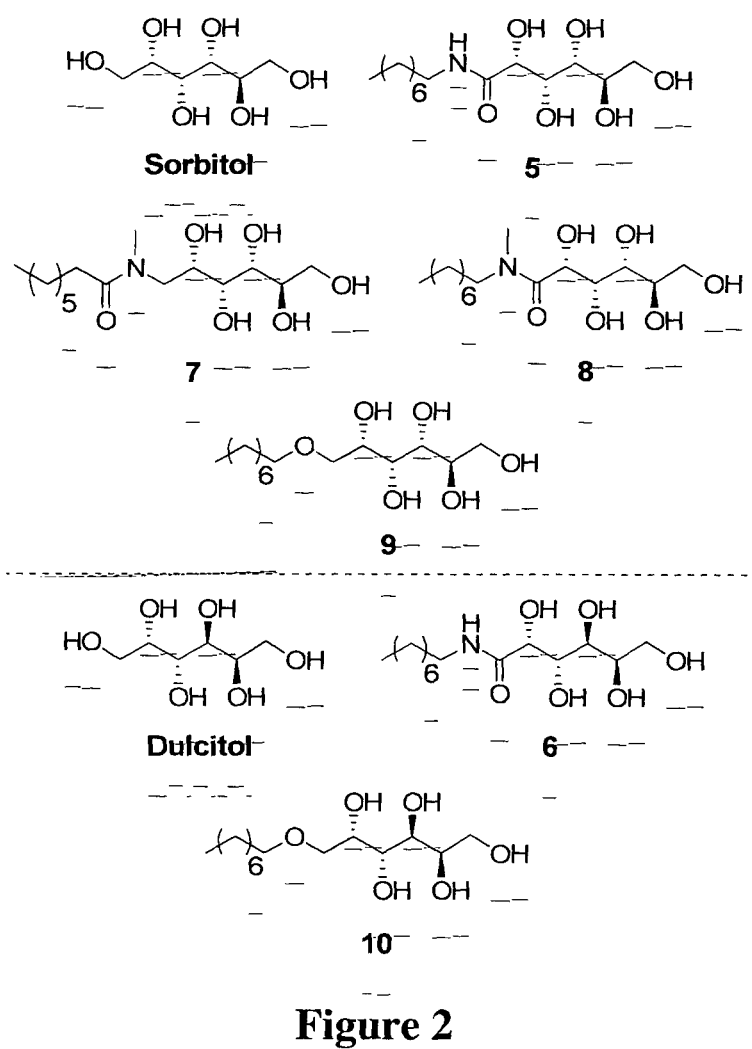
FIG. 2 is the structures of D-sorbitol, D-dulcitol, low molecular weight hydrogelator derivatives N-octyl-D-gluconamide (compound 5) and N-octyl-D-galactonamide (compound 6), N-methylated derivatives (compounds 7 and 8), and ether-linked derivatives (compounds 9 and 10).

N-Octyl-D-aldonamides, compounds 5 and 6 as shown in FIG. 2, are another class of low molecular weight carbohydrate-based compounds known to self-assemble in water. These compounds are prone to aggregation and formation of fibers and hydrogels. Their ice recrystallization inhibition activity was assessed using a "splat cooling" assay.

In this assay, the area of ice crystals are measured after a 30 minute annealing time at −6.4° C. and compared to a positive control for ice recrystallization resulting in a quantitative measurement of the mean ice grain size. For a positive control, a PBS solution was utilized. All samples were normalized to the PBS positive control.

Figure 3:
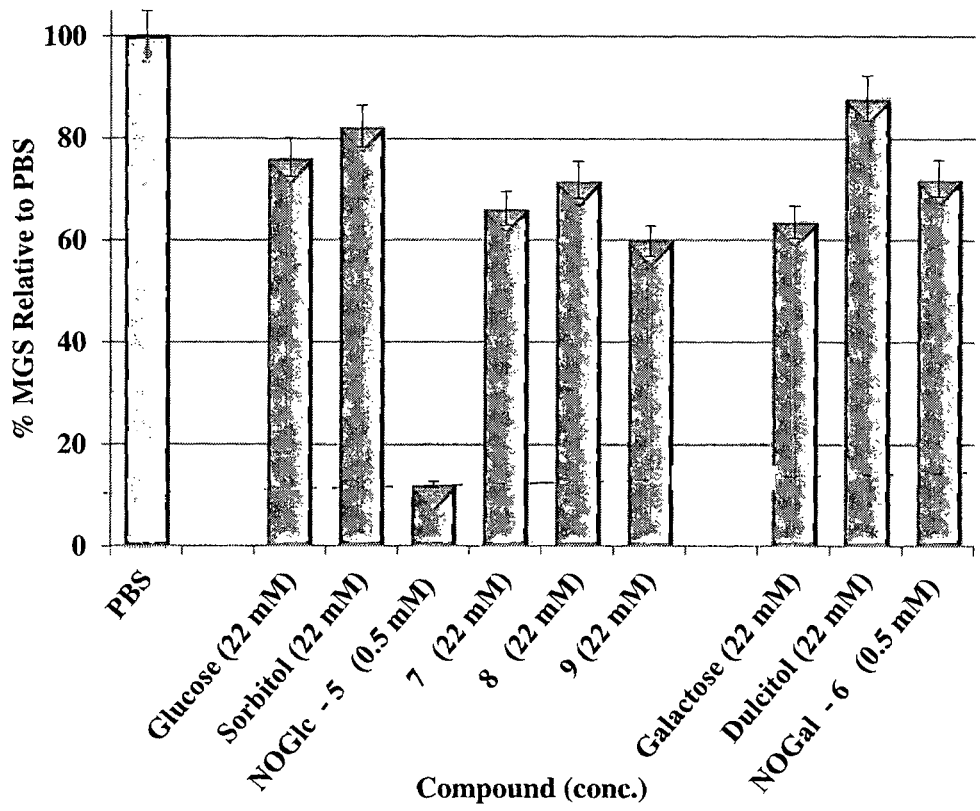
FIG. 3 is a graphical representation of ice recrystallization inhibition activity of D-sorbitol, D-dulcitol, and compounds 5-9. All compounds are represented as a % MGS (mean grain size) of ice crystals relative to the PBS positive control.
Figure 4:
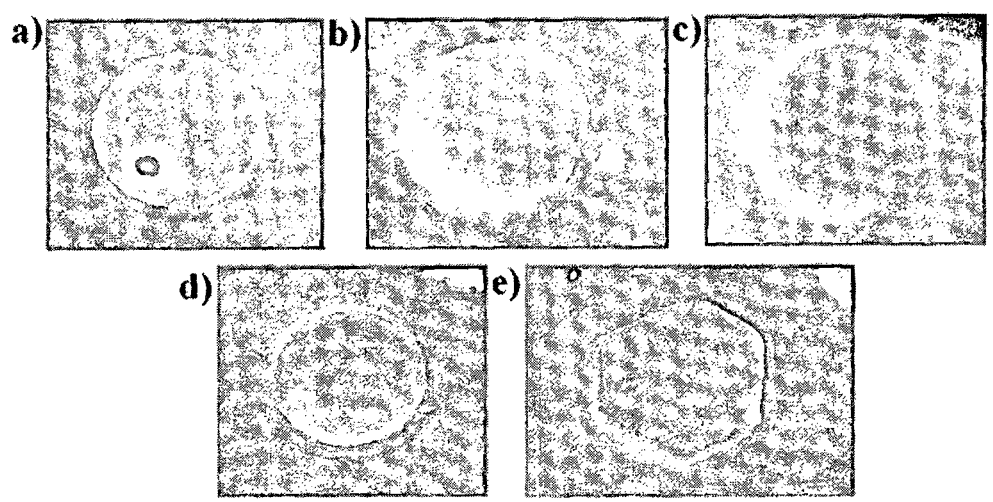
FIG. 4($a$) shows the ice crystal habits of compound 3 assayed at a concentration of 1 mg/mL.

The carbohydrate moiety of the N-octyl-D-aldonamides is in the open-chain alditol form. Therefore, prior to assessing the ice recrystallization inhibition activity of these hydrogelators, the activity of D-sorbitol and D-dulcitol and the open-chain reduced form of D-glucose and D-galactose, respectively, was assessed (as shown in FIG. 3). The importance of the pyranose ring for ice recrystallization inhibition activity is evident as both of these alditols had decreased activity relative to the pyranose forms. While hydration numbers for the pyranose forms of D-galactose and D-glucose have previously been reported, the hydration numbers for the alditols (D-dulcitol and D-sorbitol) are not known. However, it is known that the hydration of a monosaccharide is mostly dependent on the relative stereochemistry of the C2 and C4 hydroxyl groups of the pyranose ring. There is a significant decrease in ice recrystallization inhibition activity for D-dulcitol in comparison to D-galactose, and the ice recrystallization inhibition activity of both alditols (D-dulcitol and D-sorbitol) is statistically similar. Without being bound by theory, this result suggests that removal of the rigid pyranose ring of a monosaccharide directly influences hydration and results in a loss of ice recrystallization inhibition activity.

The ice recrystallization inhibition activity of low molecular weight carbohydrate-based hydrogelators, compounds 5 and 6, is shown in FIG. 3. Due to the poor solubilities associated with these compounds in water and PBS, they could only be assessed for ice recrystallization inhibition activity at 0.5 mM. Surprisingly, N-octyl-D-gluconamide (compound 5, NOGlc) exhibited potent ice recrystallization inhibition activity at 0.5 mM, while its diastereomer N-octyl-D-galactonamide (compound 6, NOGal) exhibited only moderate ice recrystallization inhibition activity. In fact, the activity of compound 6 at 0.5 mM was statistically similar to the activity of D-galactose at 22 mM. These results are highly unprecedented and are the first example where a D-glucose derivative was a more potent inhibitor of ice recrystallization than a D-galactose derivative. Furthermore, N-octyl-D-gluconamide (compound 5) is the first example of a small molecule having potent ice recrystallization inhibition activity at a significantly lower concentration than 22 mM.

Interestingly, compound 5 exhibited potent ice recrystallization inhibition activity at 0.5 mM, but compound 7 exhibited only moderate ice recrystallization inhibition activity at a higher concentration of 22 mM. Compound 8 exhibited similar ice recrystallization inhibition activity to compound 7 at 22 mM further validating the importance of the proton on the amide bond in 5 for potent ice recrystallization inhibition activity. In addition, replacement of the amide bond in D-glucose derivative 5 with an ether linkage (9) resulted in a dramatic decrease in ice recrystallization inhibition activity. Ether-linked compound 9 exhibited ice recrystallization inhibition activity similar to compounds 7 and 8 at 22 mM. Collectively, these results indicate that the amide bond of compound 5 is crucial for potent ice recrystallization inhibition activity.

Interestingly, compound 9 is the open-chain alditol derivative of the non-ionic D-glucose-based surfactant compound 3 and compound 9 was a better inhibitor of ice recrystallization than compound 3 at 22 mM (FIGS. 1 and 3). This was surprising as the ice recrystallization inhibition activity for alditols D-sorbitol and D-dulcitol (FIG. 3) was decreased in comparison to the corresponding pyranose forms of the sugars (D-glucose and D-galactose, respectively). As non-ionic D-galactose surfactant 4 exhibited potent ice recrystallization inhibition activity at 22 mM (FIG. 1), we synthesized compound 10 to further examine the influence of the alditol moiety on ice recrystallization inhibition activity. Compound 10 is the open-chain alditol derivative of compound 4. Unfortunately, even at 11 mM, compound 10 was insoluble in PBS, and thus its ice recrystallization inhibition activity could not be assessed at similar concentrations which compounds 4 and 9 were assessed.

Example 3

Interactions with the Ice Lattice

It has previously been demonstrated that C-linked AFGP analogues 1 and 2 exhibited potent ice recrystallization inhibition activity but did not possess TH activity, which suggested that the mechanism of action for these potent inhibitors of ice recrystallization is different from native AF(G)Ps as no direct interaction with the ice lattice was observed. As both compound 4 (at 22 mM) and compound 5 (at 0.5 mM) are novel potent low molecular weight inhibitors of ice recrystallization, whether they were interacting directly with the ice lattice was investigated. Carbohydrate derivatives (compounds 3-6) were examined for TH activity using a Clifton Nanoliter Osmometer. See Tam, R. et al. (2009) "Solution Conformation of C-Linked Antifreeze Glycoprotein Analogues and Modulation of Ice Recrystallization" J. Am. Chem. Soc. 131:15747-15753; Tam, R. et al. (2008) "Hydration Index—A Better Parameter for Explaining Small Molecule Hydration in Inhibition of Ice Recrystallization" J. Am. Chem. Soc. 130: 17494-17501.

In this assay a single droplet of the sample in water was suspended in the center of an oil-filled well in a sample holder plate. The sample was then rapidly frozen using a thermoelectrically controlled microscope stage, then the temperature was raised and the sample melted until only a single ice crystal remained. Once a single ice crystal was obtained, its growth and behavior upon increasing/decreasing the temperature was viewed under a microscope.

The above synthesized C-linked AFGP analogues and carbohydrate derivatives were assessed for TH activity at 10 mg/mL. Compounds 3-6 could not be assessed for TH activity at this concentration due to their amphiphilic nature. During the process of melting the frozen sample to obtain a single ice crystal, the droplet dissolved in the oil resulting in one phase. Thus, compounds 3 and 4 were assayed at a concentration of 1 mg/mL, and compounds 5 and 6 were assayed at a concentration of 0.01 mg/mL. None of these derivatives (compounds 3-6) exhibited TH activity or dynamic ice shaping at these concentrations as shown in FIGS. 4(a)-(d). The absence of dynamic ice shaping indicated there was no interaction with the ice lattice.

Many AF(G)Ps have measureable TH gaps at concentrations as low as 0.5 mg/mL. However, only hyperactive AFPs have been reported to have measureable TH activity at concentrations of 0.01-0.05 mg/mL. Therefore, native AFGP-8 was assayed at a concentration of 0.01 mg/mL for dynamic ice shaping and TH activity. While no measureable TH gap was obtained for AFGP-8 at 0.01 mg/mL, dynamic ice shaping was observed as shown FIG. 4e. This indicated that even at a low concentration of 0.01 mg/mL evidence of an interaction with the ice lattice can still be observed, even in the absence of a measurable TH gap. The fact that compounds 5 and 6 do not exhibit this activity suggests that these compounds are not interacting with the ice lattice. However, as compounds 5 and 6 could not be tested for TH activity at a concentration higher than 0.01 mg/mL, solid-state NMR was used to investigate interactions with the ice lattice.

Example 4

Solid-State NMR

Solid-state NMR has been utilized to observe the interaction of a type III AFP with ice. In this study, one of the findings was that the $^2$H spin-lattice relaxation rate ($R_1$) of frozen $D_2O$ in the presence of the AFP was much faster in comparison to the $^2H$ $R_1$ of frozen $D_2O$ on its own. It was also found that the $R_1$ of frozen $D_2O$ in the presence of ubiquitin was similar to that of frozen $D_2O$ on its own. The faster relaxation in the presence of the AFP was hypothesized to be a direct result of the AFP binding to ice as the $R_1$ of frozen $D_2O$ in the presence of the negative control, ubiquitin, was similar to that of $D_2O$ on its own, and ubiquitin does not interact with the ice lattice.

Figure 5:
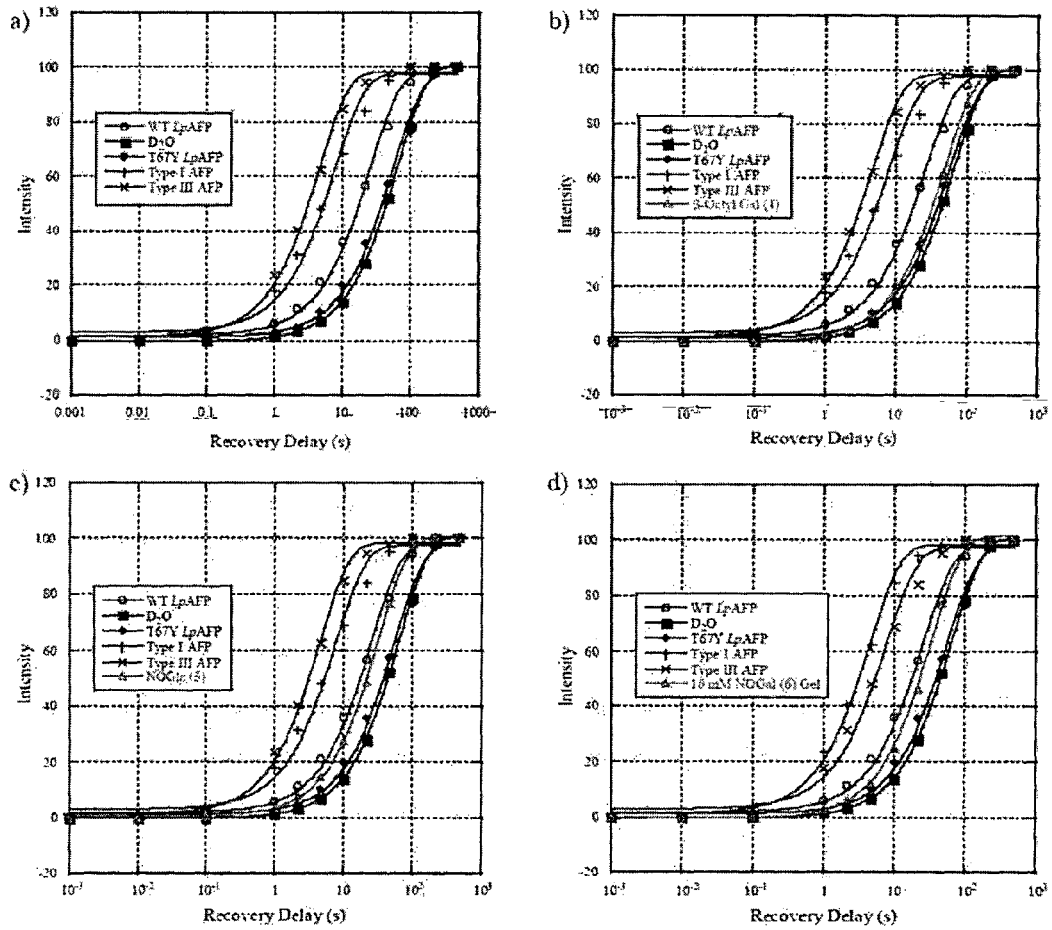
FIG. 5($a$) is a graphical representation of the saturation recovery curves of frozen $D_2O$ with the AFP controls, which were three positive controls for ice binding: Type I AFP ($R_1=0.13\pm0.01$ $s^{-1}$), Type III AFP ($R_1=0.22\pm0.01$ $s^{-1}$), WT LpAFP ($R_1=0.039\pm0.002$ $s^{-1}$); and one negative control for ice binding: T67Y LpAFP ($R_1=0.018\pm0.001$ $s^{-1}$). The $^2H$ relaxation rate for frozen $D_2O$ was $R_1=0.0154\pm0.0002$ $s^{-1}$.

Prior to measuring the $^2H$ $R_1$ of frozen $D_2O$ in the presence of compounds 3-6, the $R_1$ of pure $D_2O$ at −25° C., as well as the $R_1$ of frozen $D_2O$ in the presence of three positive controls and one negative control for ice binding was measured. The saturation recovery curves for these measurements are shown in FIG. 5a. The $^2H$ relaxation rate for frozen $D_2O$ was $R_1$=0.0154±0.0002 s$^{-1}$. Two of the positive controls chosen were a type I AFP (winter flounder, *Pseudopleuronectes americanus*) and a type III AFP (ocean pout, *Macrozoarces americanus*). As can been seen from FIG. 5a, the $R_1$ of frozen $D_2O$ with both type I ($R_1$=0.13±0.01 s$^{-1}$) and type III AFP ($R_1$=0.22±0.01 s$^{-1}$) is much faster than the $R_1$ of frozen $D_2O$ on its own. The third positive control used was the wild-type AFP of a perennial ryegrass, *Lolium perenne* (WT LpAFP) ($R_1$=0.039±0.002 s$^{-1}$). This AFP was chosen as it can be recombinantly expressed in *Escherichia coli* (*E. coli*). In addition, a mutant of this AFP (T67Y LpAFP) could be utilized as a negative control for ice binding as it has previously been demonstrated that substitution to a bulky tyrosine residue disrupted the discrete complementarity between the ice-binding face of the AFP and ice, resulting in minimal TH activity. Thus, WT LpAFP and T67Y LpAFP were recombinantly expressed in *E. coli* (Yu, S. et al. (2010) "Ice restructuring inhibition activities in antifreeze proteins with distinct differences in thermal hysteresis." Cryobiology 61(3):327-334), and the $R_1$ of frozen $D_2O$ in their presence was measured (FIG. 5a). The $R_1$ of frozen $D_2O$ with T67Y LpAFP ($R_1$=0.018±0.001 $s^{-1}$) was similar to that of frozen $D_2O$ on its own. In contrast, a significantly faster $^2H$ relaxation rate was observed in the presence of all three positive controls which are known to bind to ice.

Figure 14:
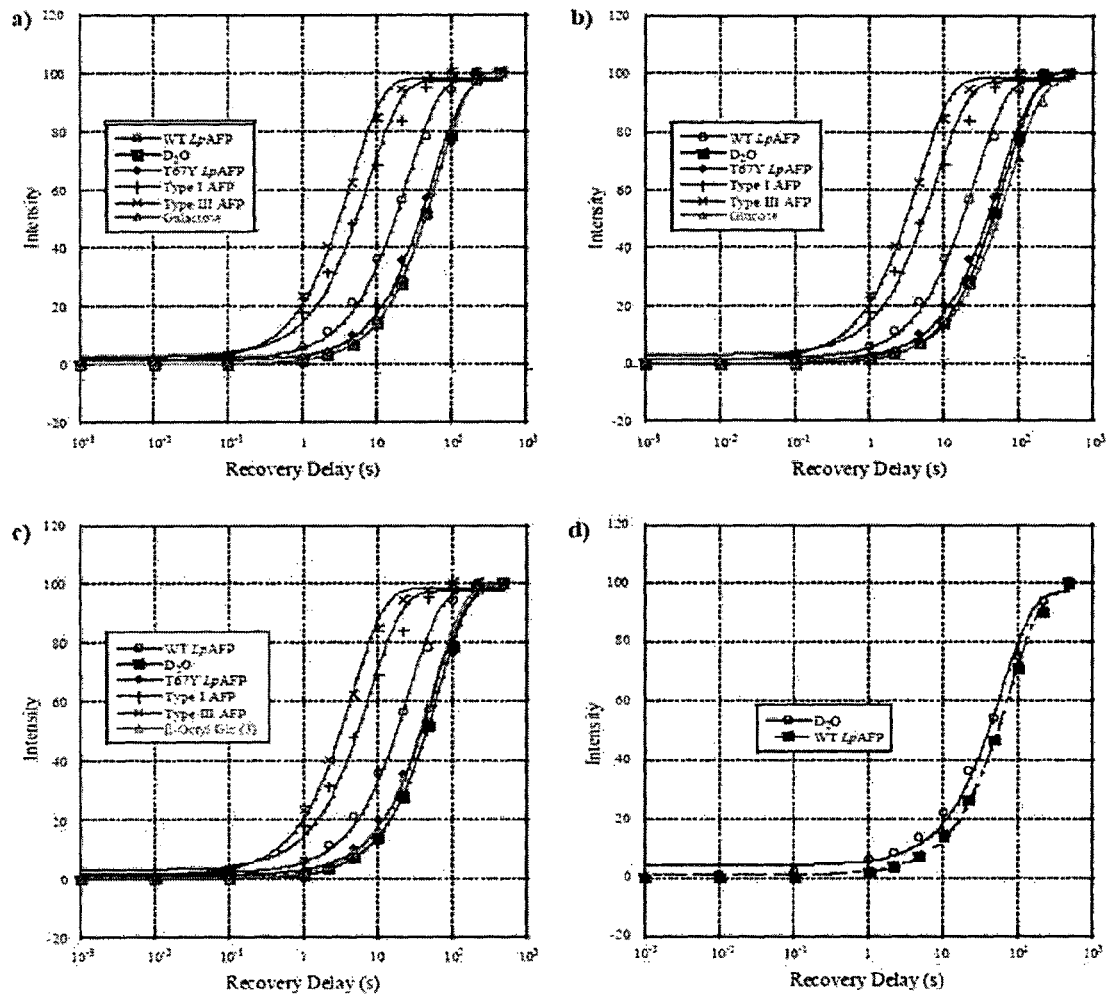
FIG. 14(a) is a graphical representation of the saturation recovery curves of frozen $D_2O$ with the AFP controls and D-galactose ($R_1=0.0154\pm0.0003$ s$^{-1}$). The concentration at which D-galactose was measured was 103 mM. The concentration of D-galactose was corrected to a total overall proton concentration of 1234 mM, unless stated otherwise.
FIG. 14(b) is a graphical representation of the saturation recovery curves of frozen $D_2O$ with the AFP controls and D-glucose ($R_1=0.0132\pm0.0001$ s$^{-1}$). The concentration at which D-glucose was measured was 103 mM. The concentration of D-D-glucose was corrected to a total overall proton concentration of 1234 mM, unless stated otherwise.
FIG. 14(c) is a graphical representation of the saturation recovery curves of frozen $D_2O$ with the AFP controls and compound 3 ($R_1=0.0190\pm0.0002$ s$^{-1}$). The concentration at which compound 3 was measured was 44 mM. The concentration of compound 3 was corrected to a total overall proton concentration of 1234 mM, unless stated otherwise.
FIG. 14(d) is a graphical representation of the saturation recovery curves of frozen $D_2O$ and WT LpAFP ($R_1=0.0133\pm0.0005$ s$^{-1}$). The concentration at which WT LpAFP was measured was 0.5 mM, which corresponds to a total overall proton concentration of 433 mM.
Figure 15A:
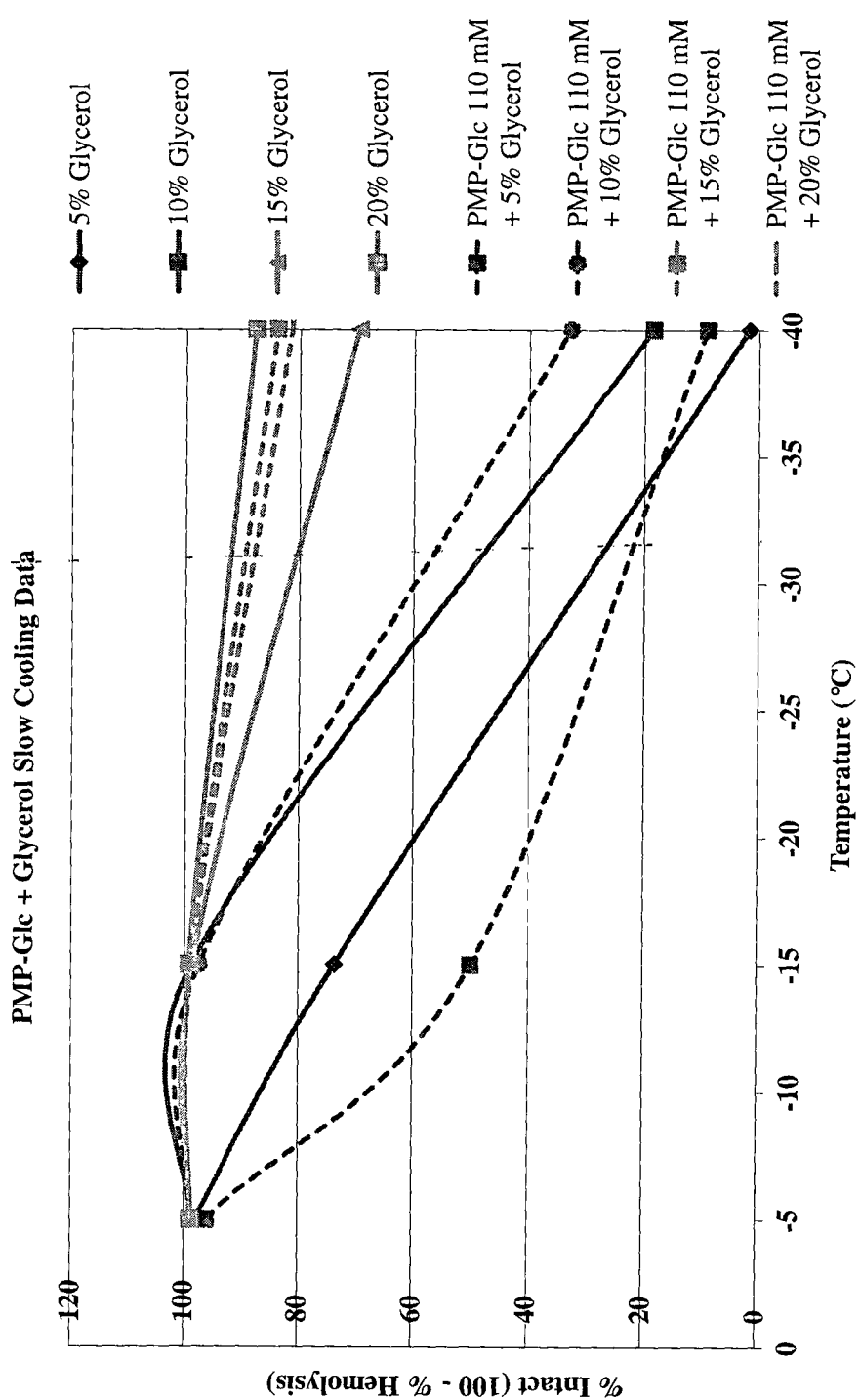
FIG. 15(a) is a graphical representation showing % intact (100-% hemolysis) v. temperature (° C.) for cryoprotectant solutions of PMP-Glc and glycerol as well as glycerol alone used to preserve red blood cells (RBCs) during slow cooling conditions.
Figure 15B:
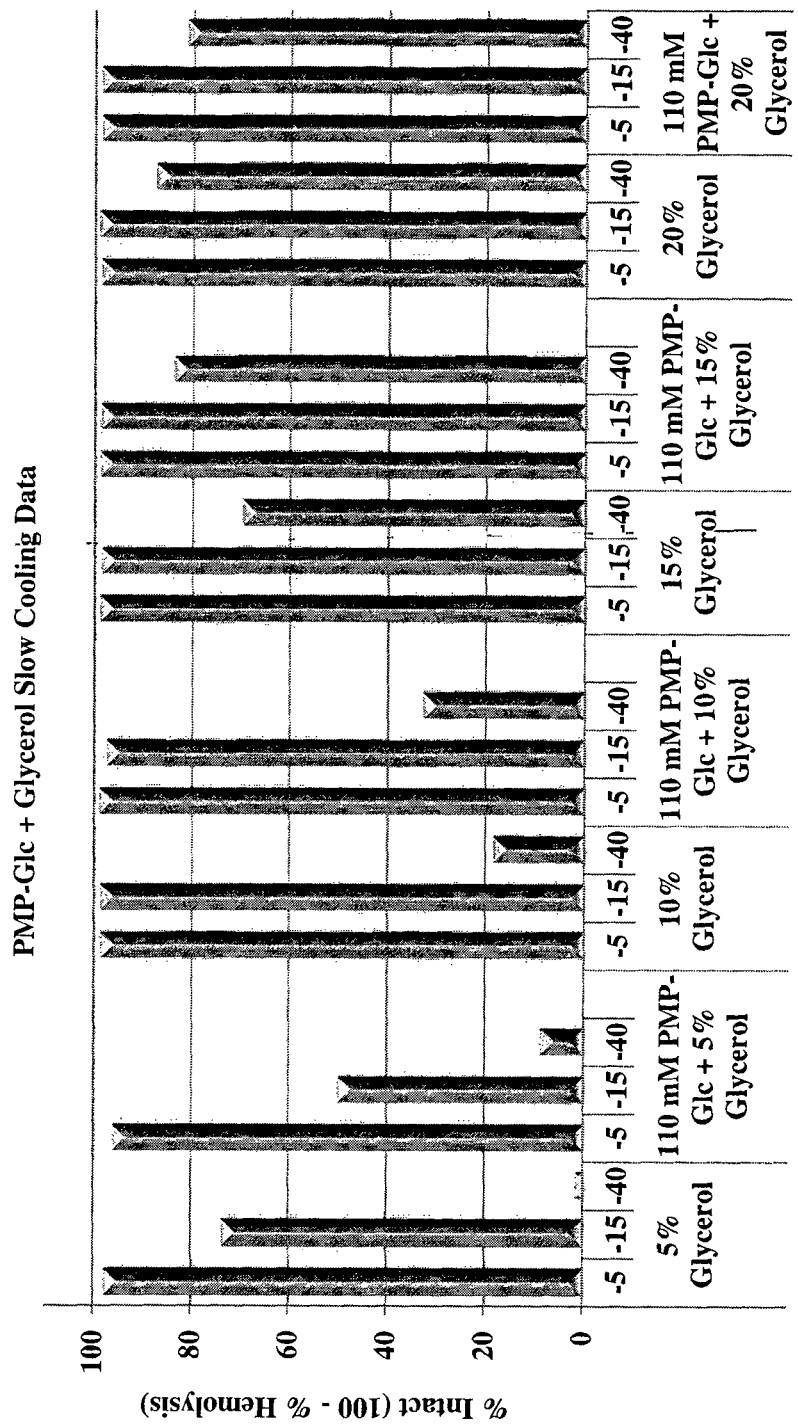
FIG. 15(b) is a graphical representation showing % intact (100-% hemolysis) for cryoprotectant solutions of PMP-Glc and glycerol as well as glycerol alone used to preserve RBCs during slow cooling conditions.
Figure 16A:
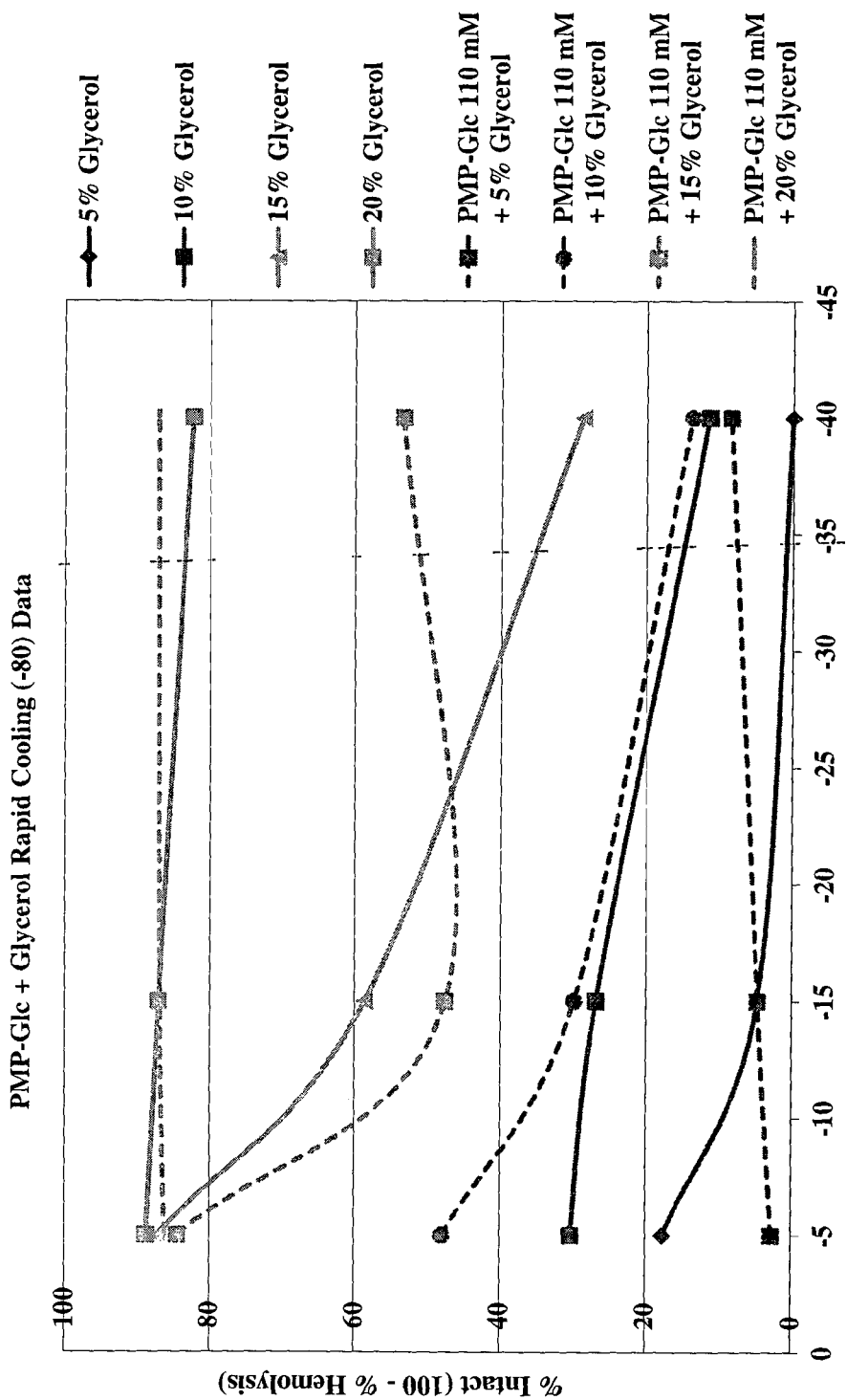
FIG. 16(a) is a graphical representation showing % intact (100-% hemolysis) v. temperature (° C.) for cryoprotectant solutions of PMP-Glc and glycerol as well as glycerol alone used to preserve RBCs during rapid cooling conditions.
Figure 16B:
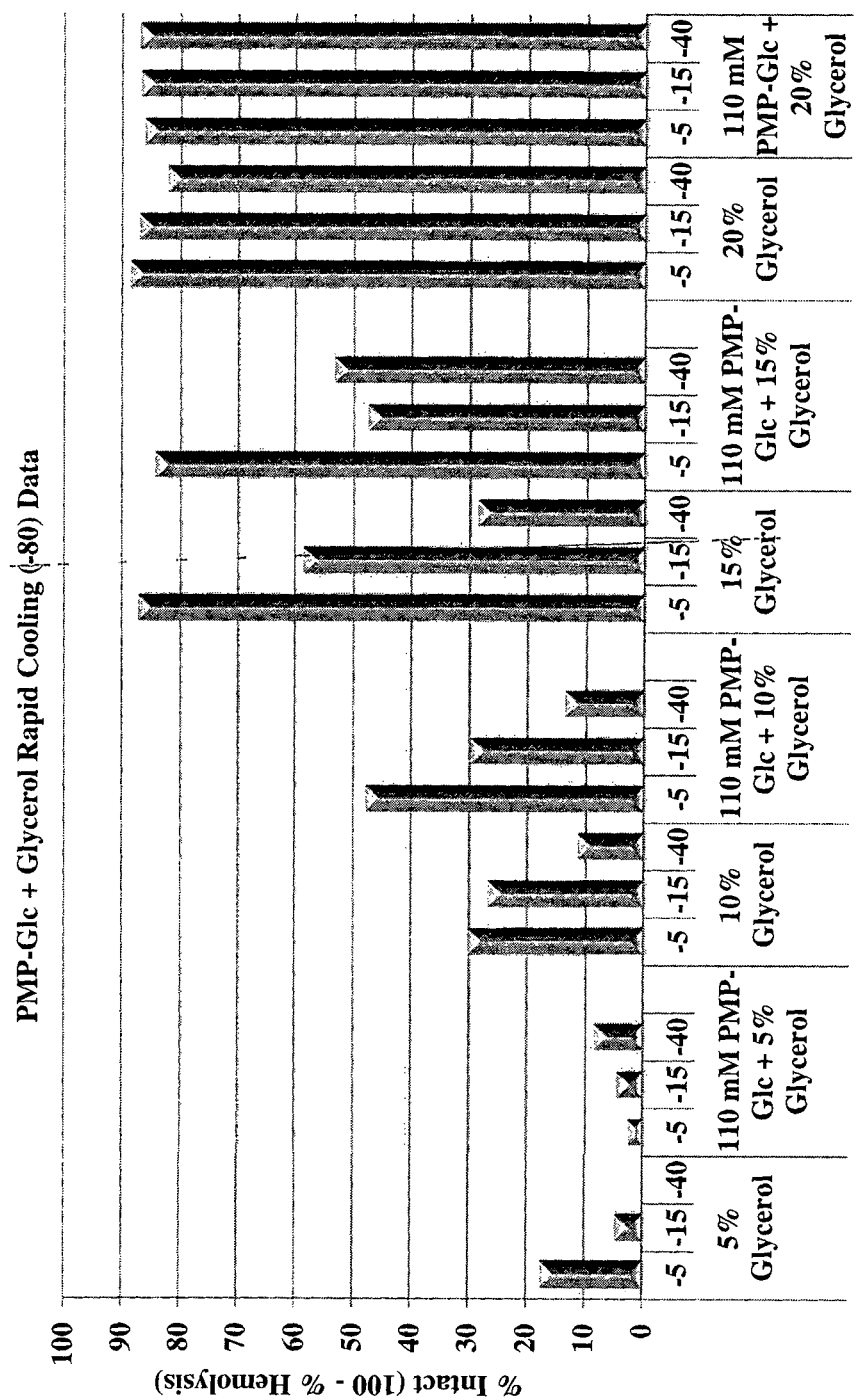
FIG. 16(b) is a graphical representation showing % intact (100-% hemolysis) for cryoprotectant solutions of PMP-Glc and glycerol as well as glycerol alone used to preserve RBCs during slow rapid conditions.
Figure 17A:
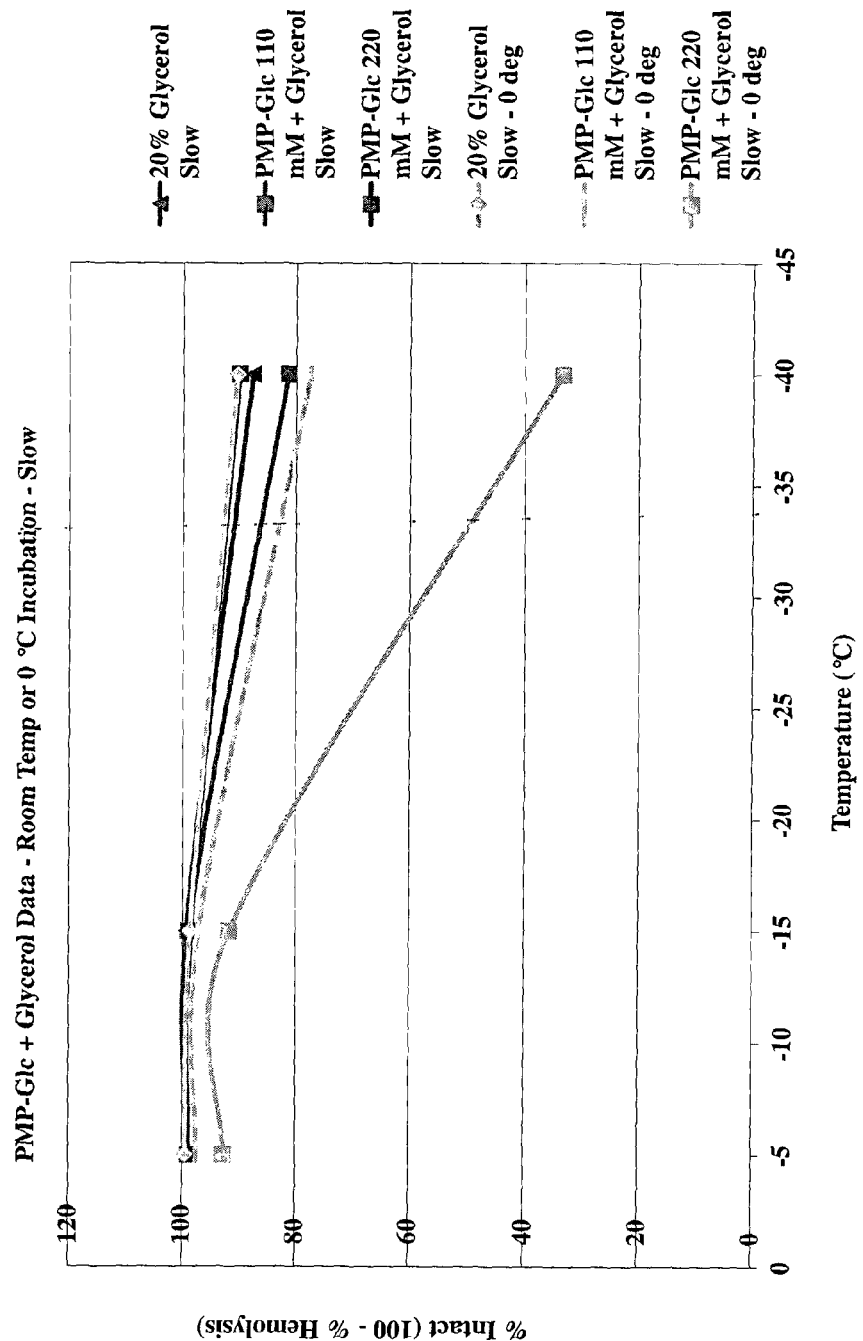
FIG. 17(a) is a graphical representation showing % intact (100-% hemolysis) v. temperature (° C.) for cryoprotectant solutions of PMP-Glc and glycerol as well as glycerol alone used to preserve RBCs during slow cooling conditions and incubation at room temperature or 0° C.
Figure 17B:
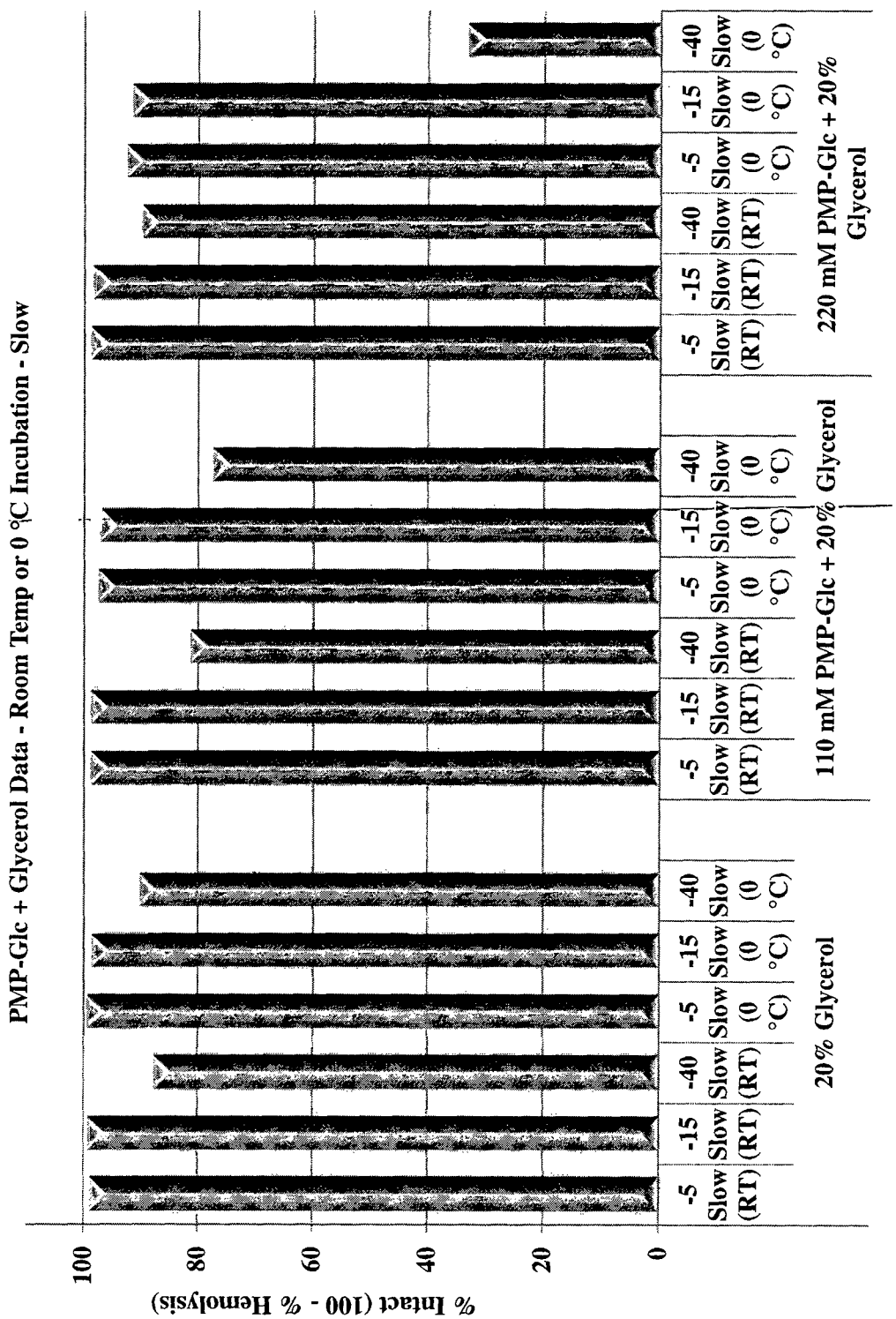
FIG. 17(b) is a graphical representation showing % intact (100-% hemolysis) for cryoprotectant solutions of PMP-Glc and glycerol as well as glycerol alone used to preserve RBCs during slow cooling conditions and incubation at room temperature or 0° C.
Figure 18A:
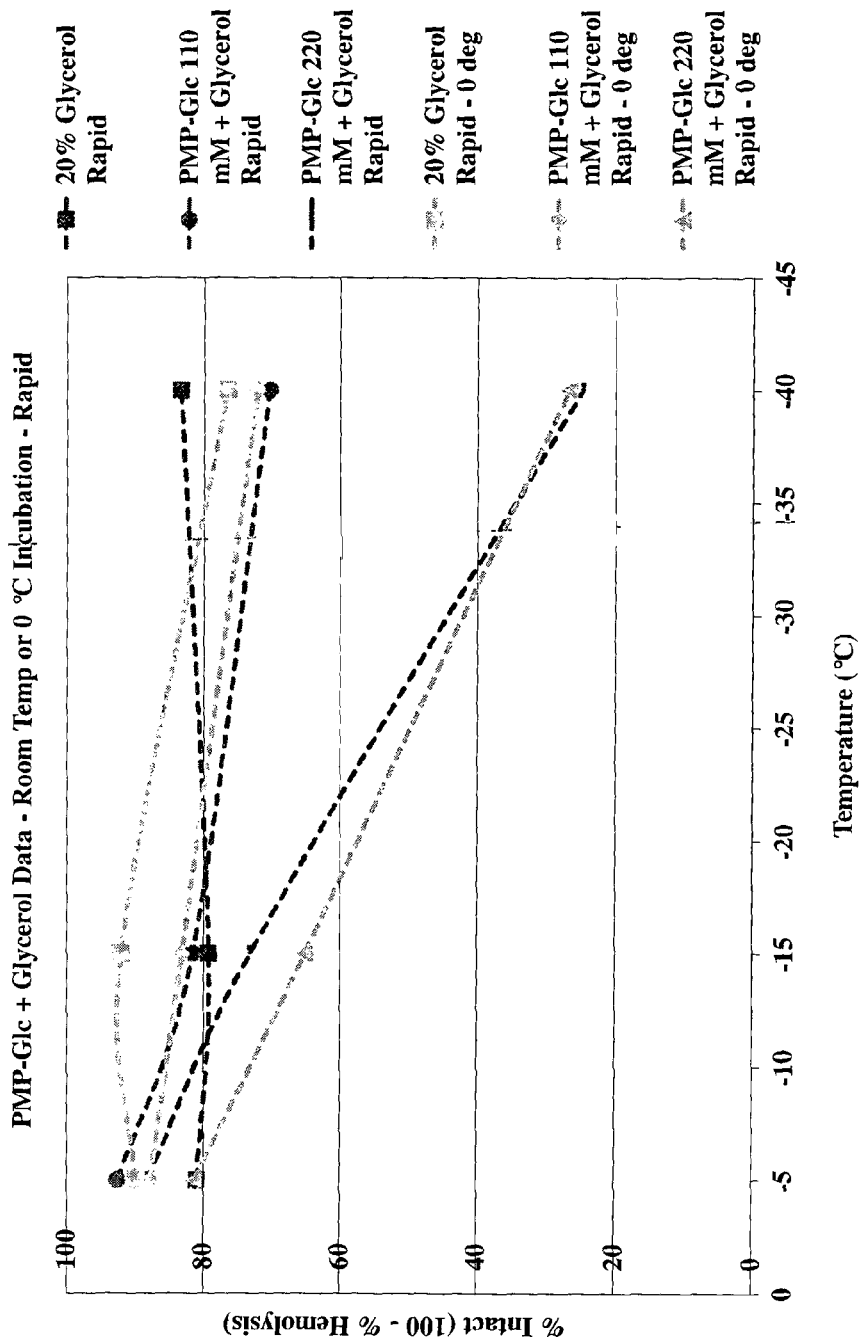
FIG. 18(a) is a graphical representation showing % intact (100-% hemolysis) v. temperature (° C.) for cryoprotectant solutions of PMP-Glc and glycerol as well as glycerol alone used to preserve RBCs during rapid cooling conditions and incubation at room temperature or 0° C.
Figure 18B:
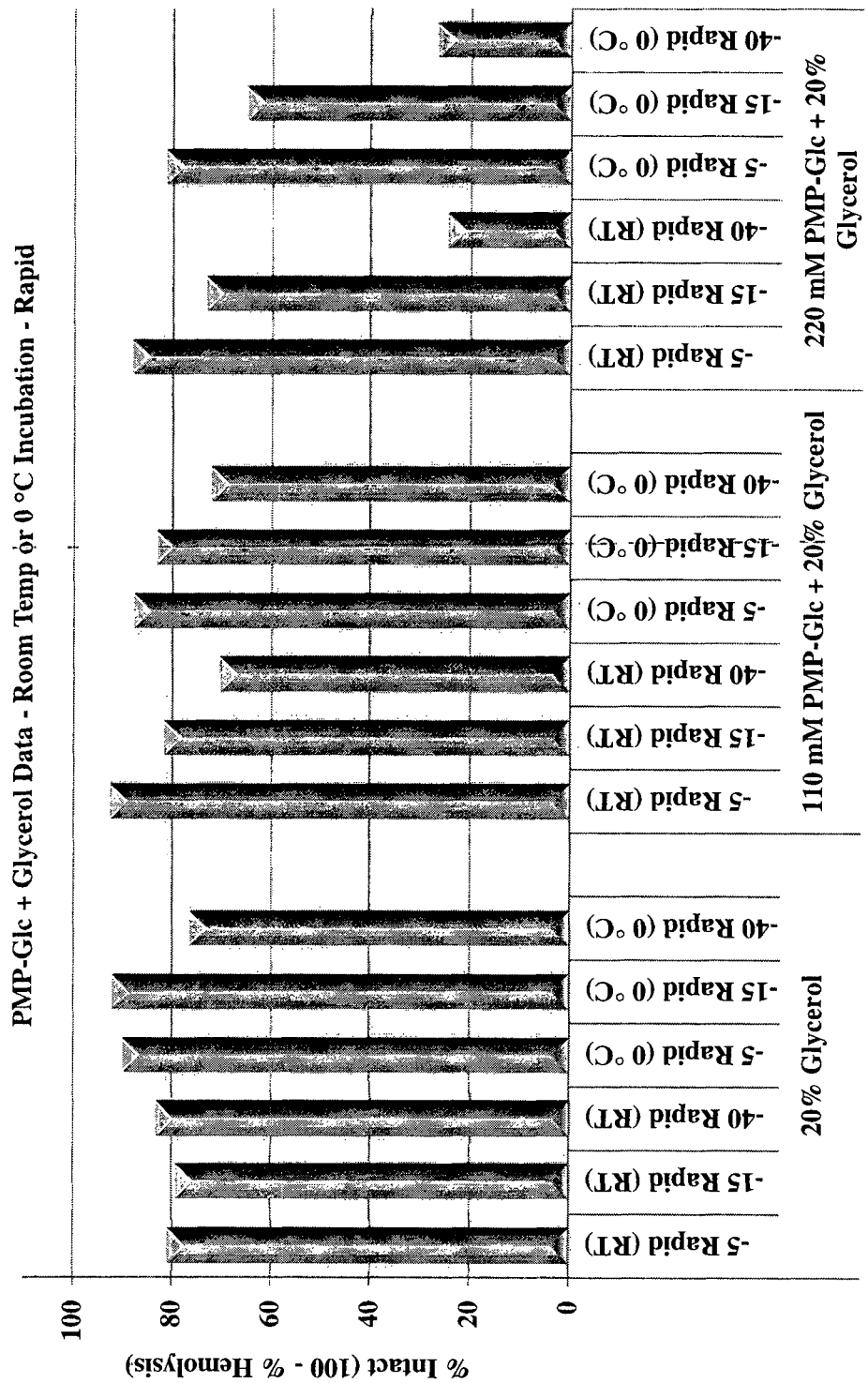
FIG. 18(b) is a graphical representation showing % intact (100-% hemolysis) for cryoprotectant solutions of PMP-Glc and glycerol as well as glycerol alone used to preserve RBCs during rapid cooling conditions and incubation at room temperature or 0° C.

Next, the saturation recovery curves of frozen $D_2O$ in the presence of compounds 3-6, as well as D-glucose and D-galactose, were recorded. All of these molecules are significantly smaller than the AFP positive controls. Therefore, to account for the drastic difference in molecular weights, the concentration which each carbohydrate derivative was measured was corrected to a total overall proton concentration of 1234 mM, the overall protein proton concentration used for the Type III AFP in the original study. As shown in FIG. 5(b), in the presence of D-galactose derivative, compound 4, the $R_1$ of frozen $D_2O$ ($R_1$=0.0209±0.0002 $s^{-1}$) was similar to that of $D_2O$ on its own, suggesting it is not interacting with the ice lattice. Similar results were also obtained for D-galactose, D-glucose, and compound 3, as shown in FIGS. 14(a)-(c), where the $R_1$ of frozen $D_2O$ in the presence of these compounds ($R_1$=0.0154±0.0003 $s^{-1}$; R1=0.0132±0.0001 $s^{-1}$; $R_1$=0.0190±0.0002 $s^{-1}$) was similar to the $R_1$ of frozen $D_2O$ on its own. These results further validated the previous TH results and suggest that the potent ice recrystallization inhibition activity of compound 4 at 22 mM is not due to an interaction with the ice lattice.

The saturation recovery curve of frozen $D_2O$ with compound 5 is shown in FIG. 5(c). Surprisingly, the $R_1$ of frozen $D_2O$ in the presence of compound 5 ($R_1$=0.0310±0.0005 $s^{-1}$) was faster than that of frozen $D_2O$ on its own. However, since the TH measurements of compound 5 indicated no dynamic ice shaping, it seemed that the faster $R_1$ was not due to an interaction with the ice lattice. As the concentration of the low molecular weight carbohydrate derivatives were corrected to a total overall proton concentration of 1234 mM, this corresponded to a 42 mM concentration of compound 5 in solution. At 42 mM, compound 5 forms a hydrogel, and so consequently the NMR measurements were conducted on a frozen hydrogel. The formation of a gel is inevitably going to be accompanied by a decrease in correlation time due to an increased mobility of the water molecules in the solid-state. This is expected to cause an increase in $R_1$, which was seen experimentally. Therefore, without being bound by theory, it is believed that the faster $R_1$ observed for frozen $D_2O$ with compound 5 is due to increased molecular motion during these measurements caused by gelation, which was further supported by the saturation recovery curve of frozen $D_2O$ with D-galactose derivative (compound 6) (FIG. 5(d)). Due to solubility problems, the highest concentration at which compound 6 could be measured was its gelation concentration of 0.5% w/v, which corresponds to a concentration of 16 mM. A similar effect to what was seen with compound 5 (FIG. 5(c)) was observed with compound 6 where the $R_1$ of $D_2O$ in the frozen hydrogel of compound 6 ($R_1$=0.030±0.001 $s^{-1}$) was faster than the $R_1$ of frozen $D_2O$ on its own (FIG. 5(d)). However, a 16 mM solution of compound 6 has a total overall proton concentration of only 479 mM and at a similar protein proton concentration with the WT LpAFP, the measured $R_1$ value ($R_1$=0.0133±0.0005 $s^{-1}$) is similar to frozen $D_2O$ on its own (FIG. 5(d)). As expected, the effect of ice binding on $R_1$ is concentration dependant. Thus, at the lower total proton concentration a faster $R_1$ was observed for the frozen hydrogel of compound 6. These results suggest that the faster relaxation rates of frozen $D_2O$ observed with compounds 5 and 6 are likely due to a gelation effect.

Interestingly, the $R_1$ values of frozen $D_2O$ in both of the hydrogels (compounds 5 and 6) are similar (FIG. 5(c)-(d)) despite their dramatic difference in ice recrystallization inhibition activity. This result further validates the hypothesis that simply the ability to form a hydrogel does not necessarily result in potent ice recrystallization inhibition activity. Regardless of concentration, both compounds 5 and 6 were studied as frozen hydrogels in the solid-state NMR experiments, and both had the same relative increase in the relaxation rate of frozen $D_2O$. However, only D-glucose derivative, compound 5, had potent ice recrystallization inhibition activity (FIG. 3).

Example 5

Human Liver Cell Viability

Human liver cell viability in PMP-glucoside (compound 17, PMP-Glc) and N-octyl-D-gluconamide (compound 5, NOGlc) was assessed using a MTT Assay.

Figure 12:
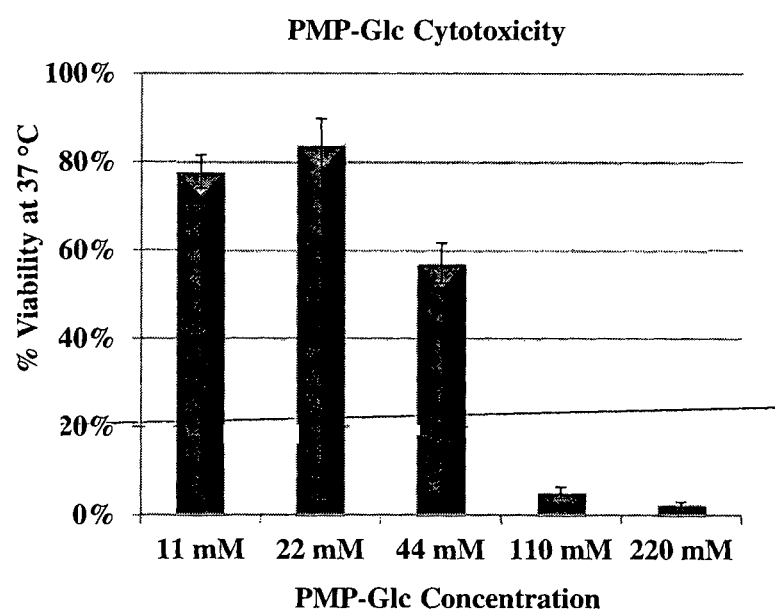
FIG. 12 is a graphical representation of the HepG2 cell viability of PMP-glucoside.
Figure 13:
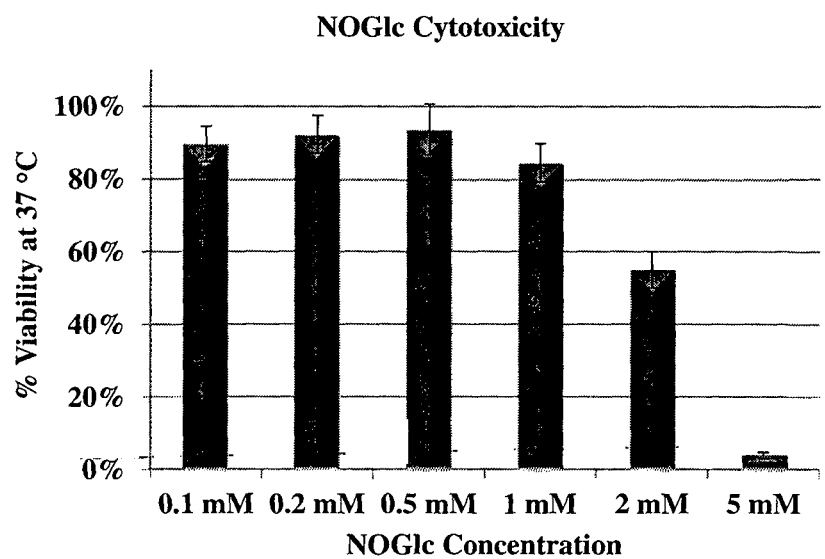
FIG. 13 is a graphical representation of the HepG2 cell viability of n-octyl-gluconamide.
Figure 25:
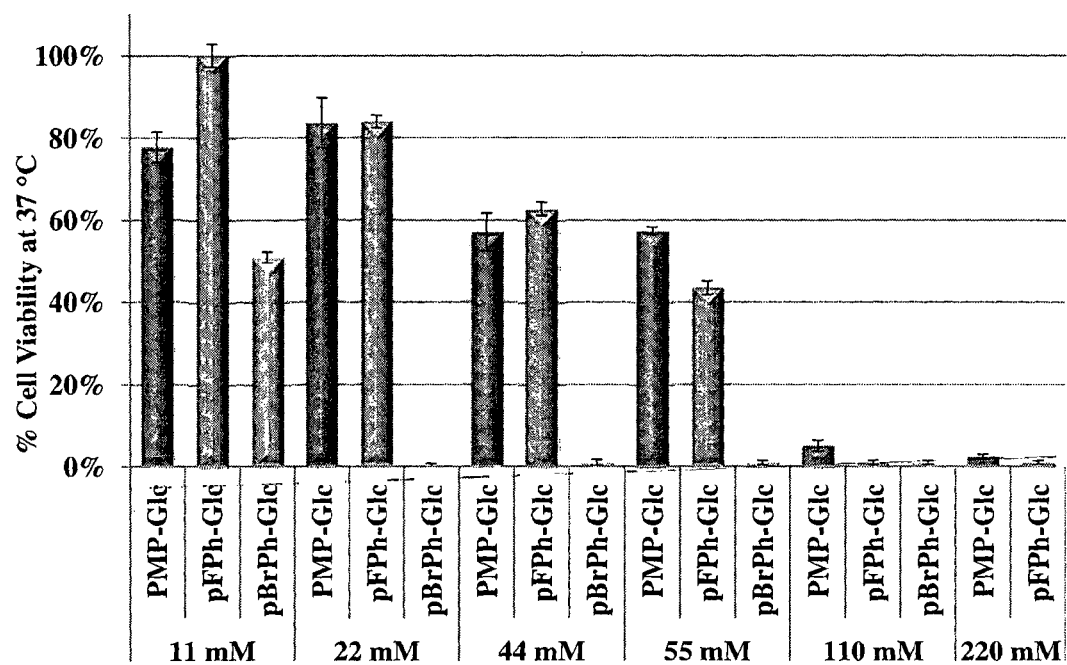
FIG. 25 is a graphical representation of the HepG2 cell viability with a cryoprotectant solution of PMP-glucose, pFPh-Glc and pBrPh-Glc at different concentrations.

In the assay, HepG2 cells (human hepatocellular carcinoma cells) were harvested and incubated at 37° C. overnight in a 96-well plate to a concentration of 20,000 cells per well using Minimum Essential Medium (MEM) as media. The following day (or once cells were confluent) the media was removed and cells were incubated at 37° C. overnight with MEM supplemented with desired concentration of PMP-Glc and NOGlc (100 µL of solution added). The following day the plates were centrifuged (700 RPM for 3 minutes) and the solutions were removed. 200 µL of MEM was added to each well, followed by 50 µL of 2.5 mg/mL MTT solution in Hank's Balanced Salt Solution (HBSS) to a final concentration of 0.5 mg/mL MTT per well. Then the plates were incubated for 3 hours at 37° C. After incubation, the plates were centrifuged (700 RPM for 3 minutes) and 200 µL of a 10% TritonX/0.1 N HCl in isopropanol solution was added to each well. The plates were incubated in the dark for 1 hour, then shaken and the absorbance at 570 nM of each well was read. % viability at 37° C. of PMP-Glc at a concentration 11 mM, 22 mM, 44 mM, 110 mM and 220 mM PMP-Glc was measured, and the results are shown in FIG. 12. % viability at 37° C. of NOGlc at a concentration of 0.1 mM, 0.2 mM, 0.5 mM, 1 mM, 2 mM and 5 mM was measured. The results are shown in FIG. 13. Also, % viability at 37° C. of PMP-Glc, pFPh-Glc and pBrPh-Glc at a concentration of 11 mM, 22 mM, 44 mM, 55 mM, 110 mM and 220 mM was measured under the same conditions for the MTT Assay described above. The results are shown in FIG. 25.

Example 6

Red Blood Cell Cryopreservation

The cryopreservation ability of various carbohydrates and carbohydrate derivatives with and without the addition of glycerol as cryoprotectants with red blood cells (RBCs) obtained from peripheral blood was assessed. Hematocrits and % hemolysis (obtained by Drabkin's assay) were analyzed for non-nucleated samples and post-thaw samples that were frozen under slow and rapid cooling conditions. A summary of the cryoprotectant solutions with the freezing temperatures analyzed is shown in Table 1 below.

Fresh whole blood was obtained then centrifuged at 1000 g for 10 minutes at 4° C. The supernatant was then removed, which included plasma, platelets and white blood cells. The RBCs were then washed with a saline solution and then centrifuged to concentrate the cells. Concentrated RBCs were then split into 1.5 mL Eppendorf tubes, with 350 µL of RBCs added to each (1 Eppendorf tube per cryo-solution for each freezing temperature analyzed). 350 µL of desired cryoprotectant was added to each tube. The cells were then incubated at room temperature or 0° C. for 10 minutes, then 300 µL of RBC/cryo-solution mixture was transferred to cryogenic tubes, with each sample being run in duplicate (300 μL×2 for each cryosolution and each freezing temperature).

The cryogenic tubes were then placed in a pre-cooled ethylene glycol bath at −5° C. and were held at this temperature for 5 minutes. After 5 minutes, duplicate non-nucleated samples for each cryo-solution were removed from the bath (−5° C. non-nuc for each cryo-solution). The samples remaining in the bath were then nucleated and held at −5° C. for 5 minutes. After this time, duplicate samples for each cryo-solution were removed and immediately thawed and analyzed for % hemolysis (−5° C. slow), and duplicate samples for each cryo-solution were placed in liquid nitrogen or packed in dry ice then placed in −80° C. freezer (−5° C. rapid, to either −196° C. (liq. $N_2$) or −80° C. (dry ice)).

The samples remaining in the bath were then cooled at a rate of 1° C. Samples were removed at −15° C. and −40° C. and were either immediately thawed and analyzed for % hemolysis (−15° C. slow and −40° C. slow) or were placed in liquid nitrogen or packed in dry ice then placed in −80° C. freezer (−15° C. rapid and −40° C. rapid, to either −196° C. (liq. $N_2$) or −80° C. (dry ice)). Samples done under rapid cooling conditions remained in liquid nitrogen or −80° C. freezer for a minimum time of 30 minutes then were thawed and analyzed for % hemolysis.

For cryoprotectant solutions 1-23 in Table 1, rapid conditions used were placing samples into liquid nitrogen. For cryoprotectant solutions 24-31, rapid conditions used were placing samples into dry ice for 5 minutes then placing in −80° C. freezer.

In cryoprotectant solutions 5-8, OGG-Gal refers to analog 1 described above. Each cryoprotectant solution was tested at each corresponding freezing temperature listed. For example, cryoprotectant solution 1, (i.e. RBCs+2 mM NOGlc+20% glycerol) was tested at −5° C. non-nuc, −5° C. slow, −5° C. rapid, −15° C. slow and −15° C. rapid.

TABLE 1

| Cryoprotectant Solutions | Freezing Temperatures |
| --- | --- |
| 1) RBCs + 2 mM NOGlc + 20% glcerol, | −5° C. non-nuc |
| 2) RBCs + 2 mM NOGlc, | −5° C. slow |
| 3) RBCs + 5 mM NOGlc + 20% glycerol, | −5° C. rapid |
| 4) RBCs + 5 mM NOGlc | −15° C. slow |
|  | −15° C. rapid |
| 5) RBCs + 2 mg/mL OGG-Gal + 20% glycerol, | −5° C. non-nuc |
| 6) RBCs + 2 mg/mL OGG-Gal, | −5° C. slow |
| 7) RBCs + 5 mg/mL OGG-Gal + 20% glycerol, | −5° C. rapid |
| 8) RBCs + 5 mg/mL OGG-Gal | −40° C. slow |
|  | −40° C. rapid |
| 9) RBCs + 220 mM Sucrose + 20% glycerol, | −5° C. non-nuc |
| 10) RBCs + 220 mM Sucrose, | −5° C. slow |
| 11) RBCs + 500 mM Sucrose + 20% glycerol, | −5° C. rapid |
| 12) RBCs + 500 mM Sucrose, | −15° C. slow |
| 13) RBCs + 220 mM Fructose + 20% glycerol, | −15° C. rapid |
| 14) RBCs + 220 mM Fructose, | −40° C. slow |
| 15) RBCs + 500 mM Fructose + 20% glycerol, | −40° C. rapid |
| 16) RBCs + 500 mM Fructose, |  |
| 17) RBCs + 110 mM PMP-Glc + 20% glycerol, |  |
| 18) RBCs + 110 mM PMP-Glc, |  |
| 19) RBCs + 220 mM PMP-Glc + 20% glycerol, |  |
| 20) RBCs + 220 mM PMP-Glc, |  |
| 21) RBCs + 20% glycerol + 110 mM PMP-Glc (incubation at room temperature or 0° C.), |  |
| 22) RBCs + 20% glycerol (incubation at room temperature or 0° C.), |  |
| 23) RBCs + 20% glycerol + 220 mM PMP-Glc (incubation at room temperature or 0° C.) |  |
| 24) RBCs + 5% glycerol + 110 mM PMP-Glc, |  |
| 25) RBCs + 10% glycerol + 110 mM PMP-Glc, |  |
| 26) RBCs + 15% glycerol + 110 mM PMP-Glc, |  |
| 27) RBCs + 20% glycerol + 110 mM PMP-Glc, |  |
| 28) RBCs + 5% glycerol, |  |
| 29) RBCs + 10% glycerol, |  |

TABLE 1-continued

| Cryoprotectant Solutions | Freezing Temperatures |
| --- | --- |
| 30) RBCs + 15% glycerol, |  |
| 31) RBCs + 20% glycerol, |  |

Figure 19A:
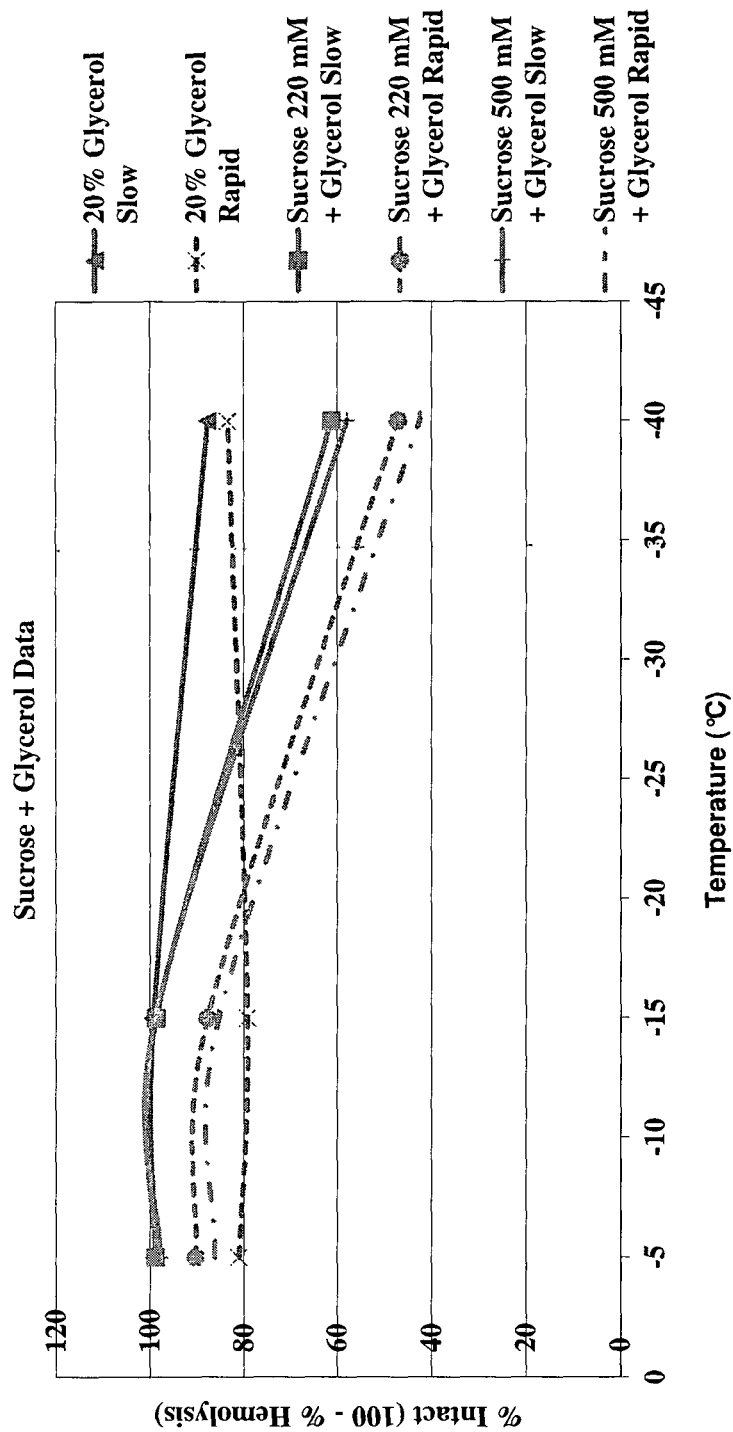
FIG. 19(a) is a graphical representation showing % intact (100-% hemolysis) v. temperature (° C.) for cryoprotectant solutions of sucrose and glycerol as well as glycerol alone used to preserve RBCs during slow and rapid cooling conditions.
Figure 19B:
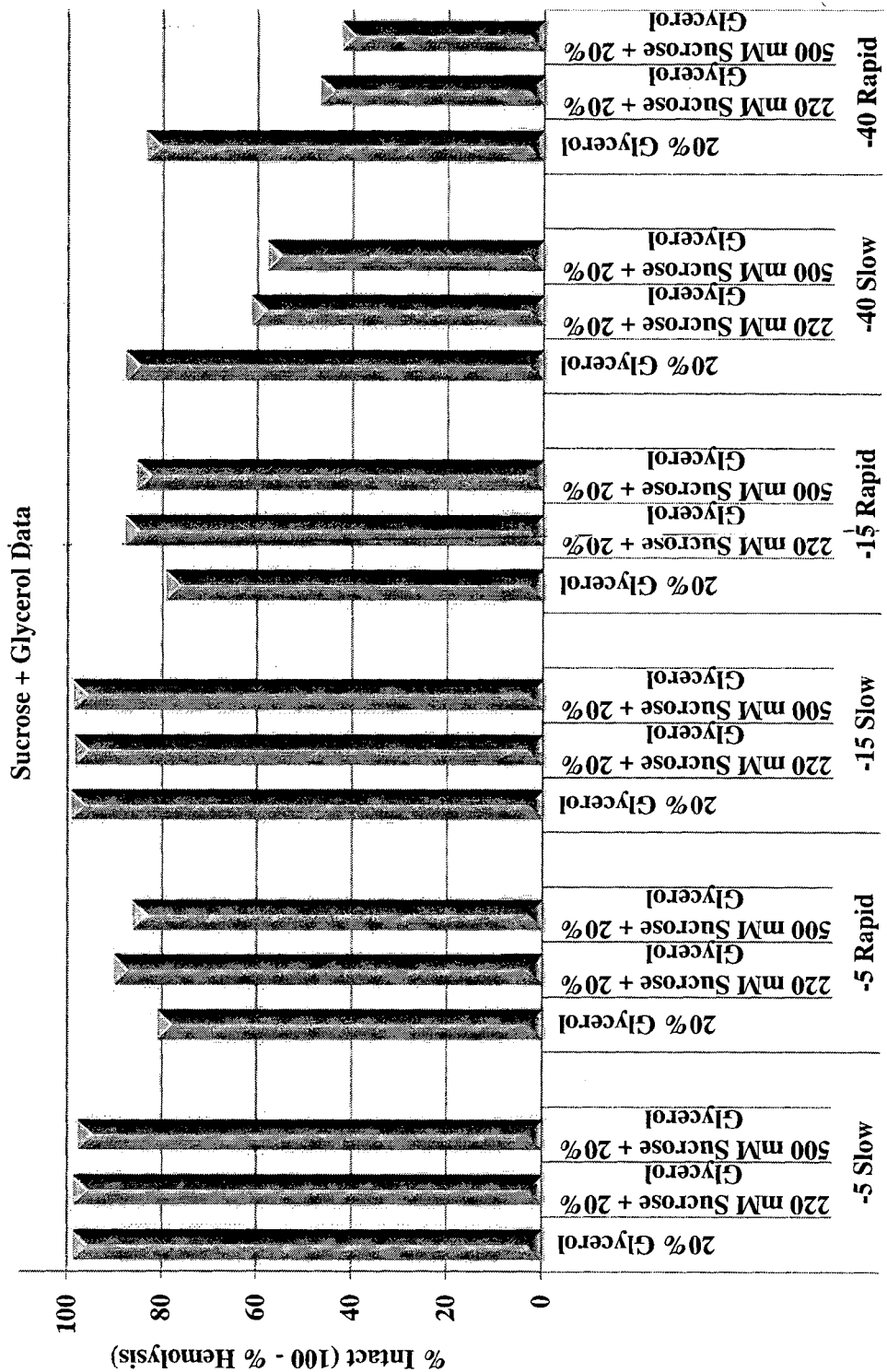
FIG. 19(b) is a graphical representation showing % intact (100-% hemolysis) for cryoprotectant solutions of sucrose and glycerol as well as glycerol alone used to preserve RBCs during slow and rapid cooling conditions.
Figure 20A:
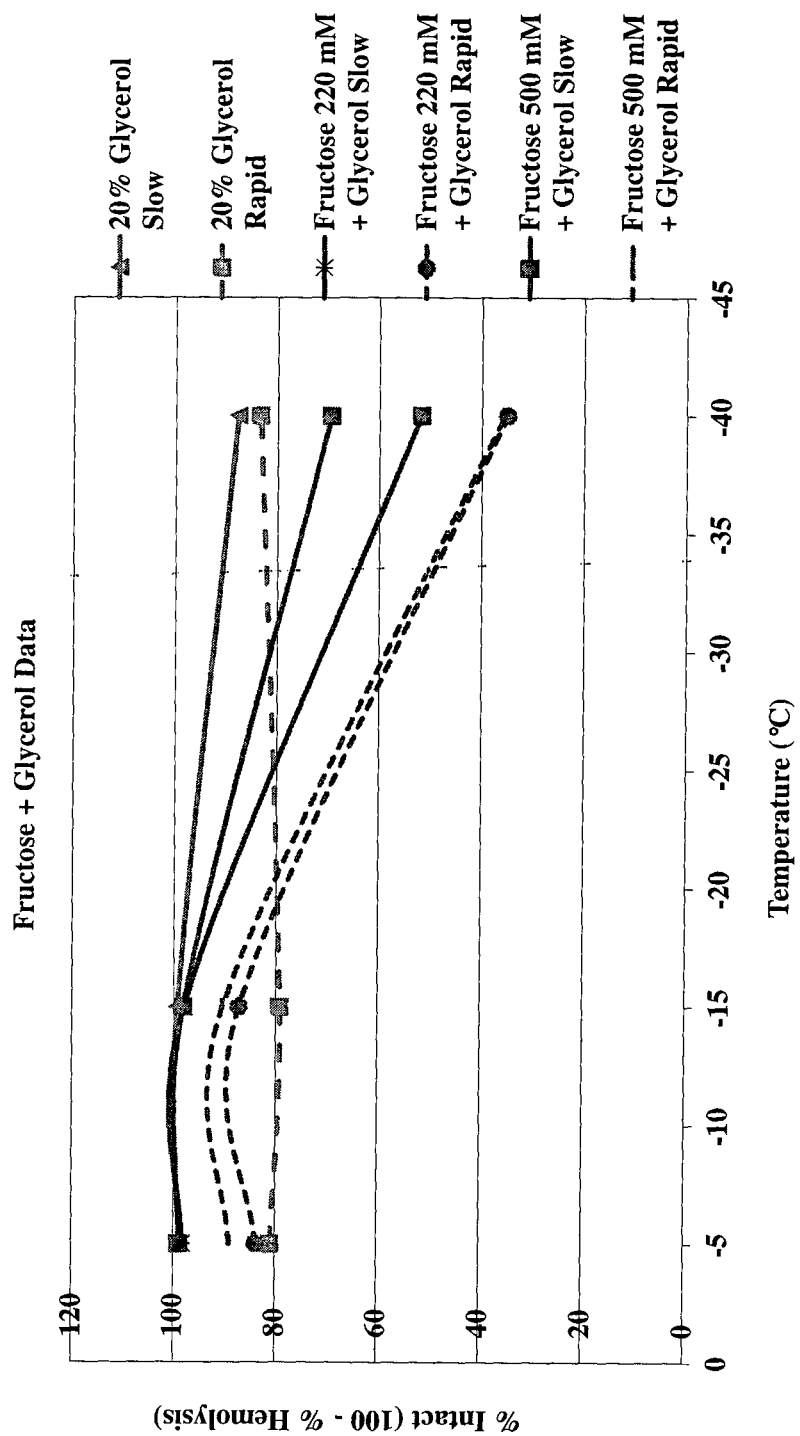
FIG. 20(a) is a graphical representation showing % intact (100-% hemolysis) v. temperature (° C.) for cryoprotectant solutions of fructose and glycerol as well as glycerol alone used to preserve RBCs during slow and rapid cooling conditions.
Figure 20B:
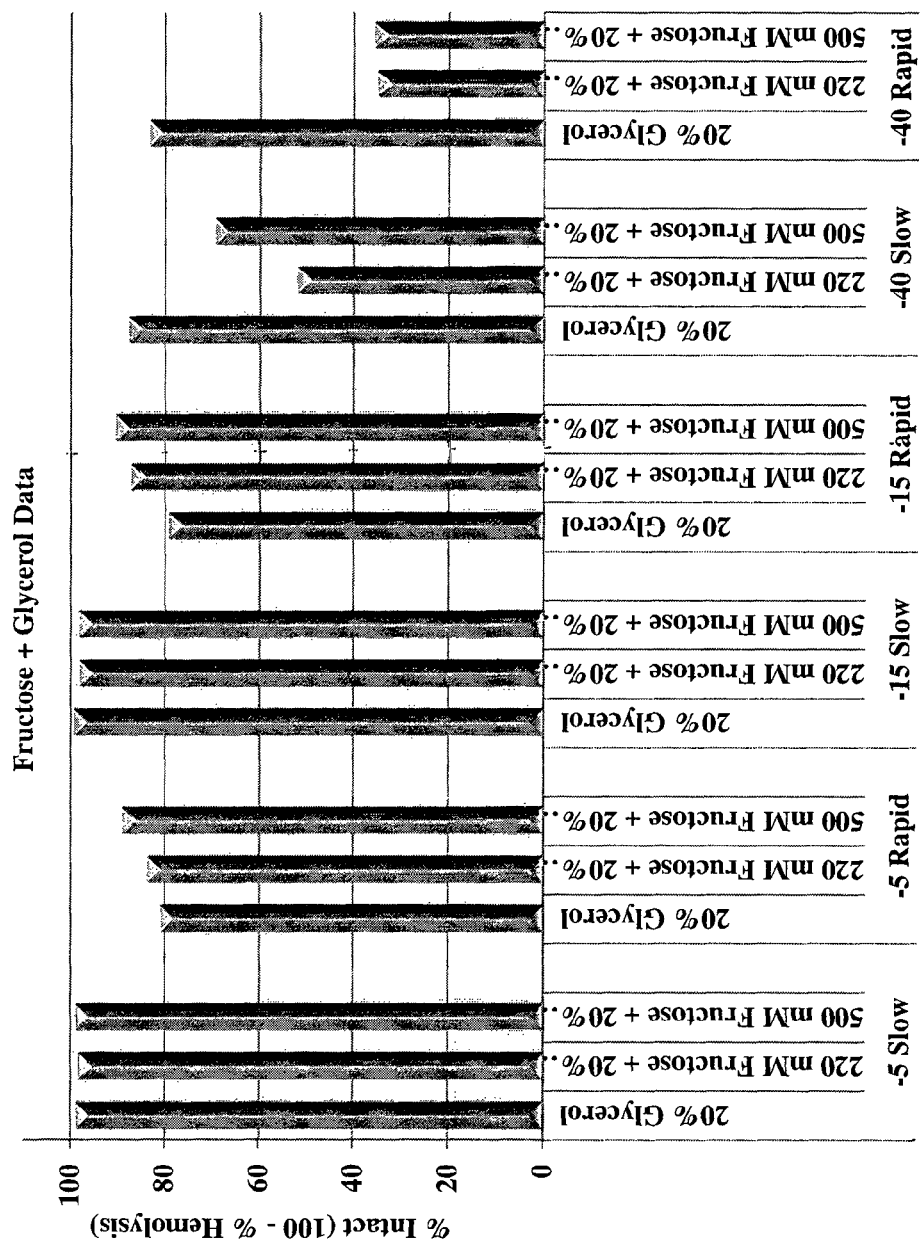
FIG. 20(b) is a graphical representation showing % intact (100-% hemolysis) for cryoprotectant solutions of fructose and glycerol as well as glycerol alone used to preserve RBCs during slow and rapid cooling conditions.
Figure 21A:
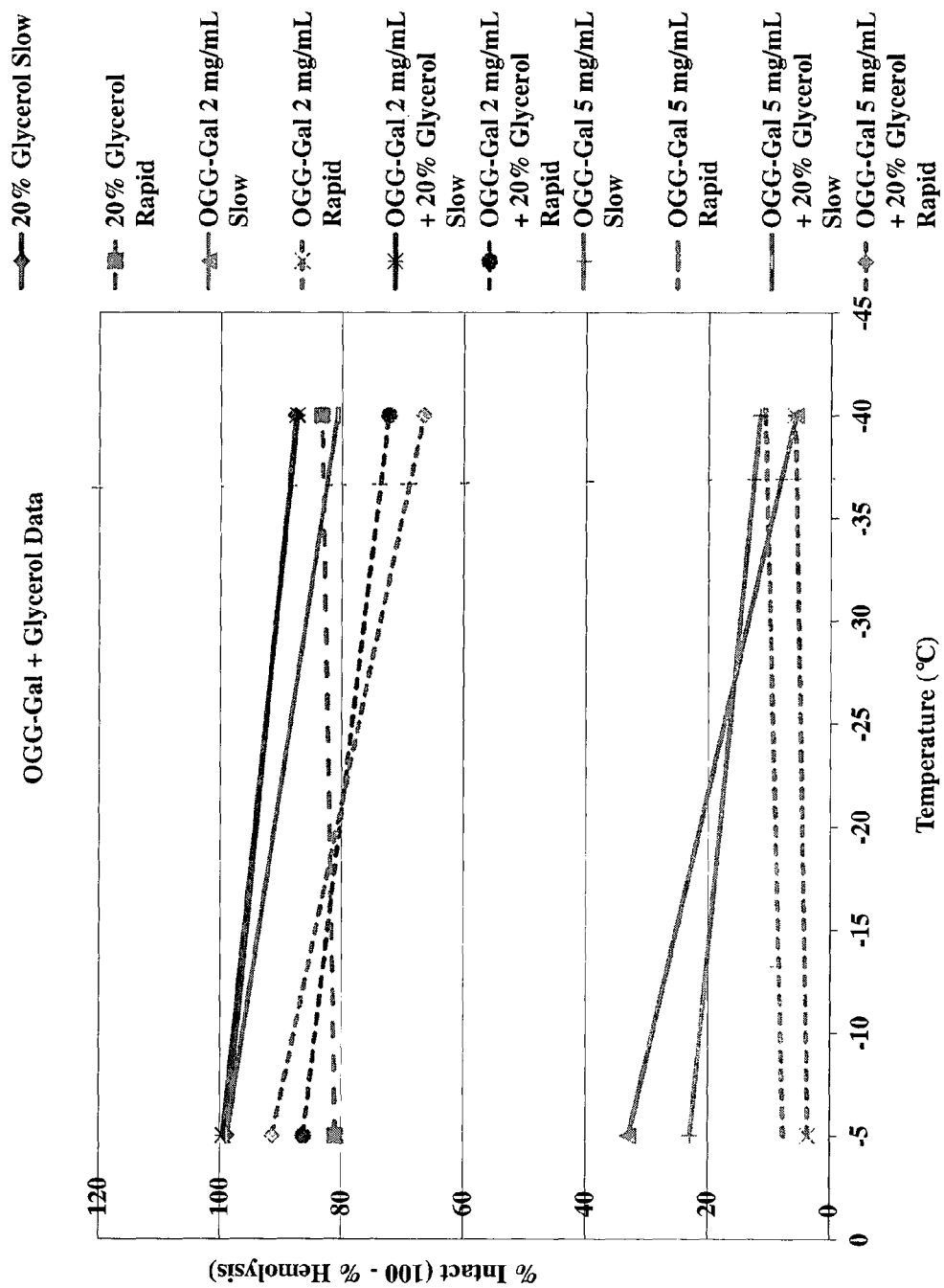
FIG. 21(a) is a graphical representation showing % intact (100-% hemolysis) v. temperature (° C.) for cryoprotectant solutions of OGG-Gal and glycerol as well as glycerol alone used to preserve RBCs during slow and rapid cooling conditions.
Figure 21B:
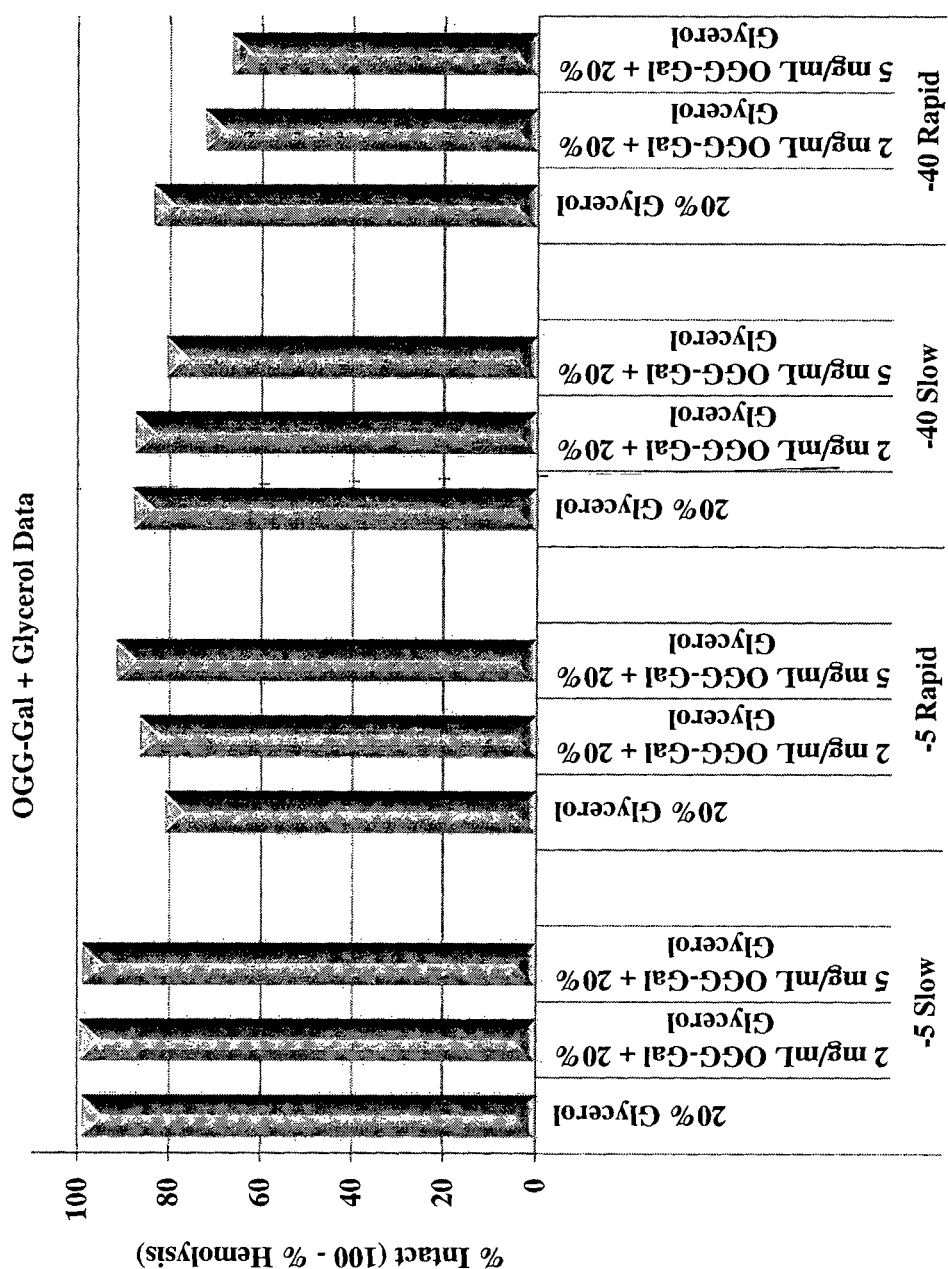
FIG. 21(b) is a graphical representation showing % intact (100-% hemolysis) for cryoprotectant solutions of OGG-Gal and glycerol as well as glycerol alone used to preserve RBCs during slow and rapid cooling conditions.

The results showing cryoprotection ability of the cryoprotectant solution of PMP-Glc with a range of concentrations of glycerol is shown in FIGS. 15-18. The results showing cryoprotection ability of the cryoprotectant solution of sucrose is shown in FIG. 19. The results showing cryoprotection ability of the cryoprotectant solution of fructose is shown in FIG. 20. The results showing cryoprotection ability of the cryoprotectant solution of OGG-Gal is shown in FIG. 21. The results showing cryoprotection ability of the cryoprotectant solution of 110 mM PMP-Glc is shown in parallel to cryoprotectant solutions of 110 mM pFPh-Glc and 55 mM pBrPh-Glc under different sets of conditions in FIGS. 22 and 23.

Figure 22:
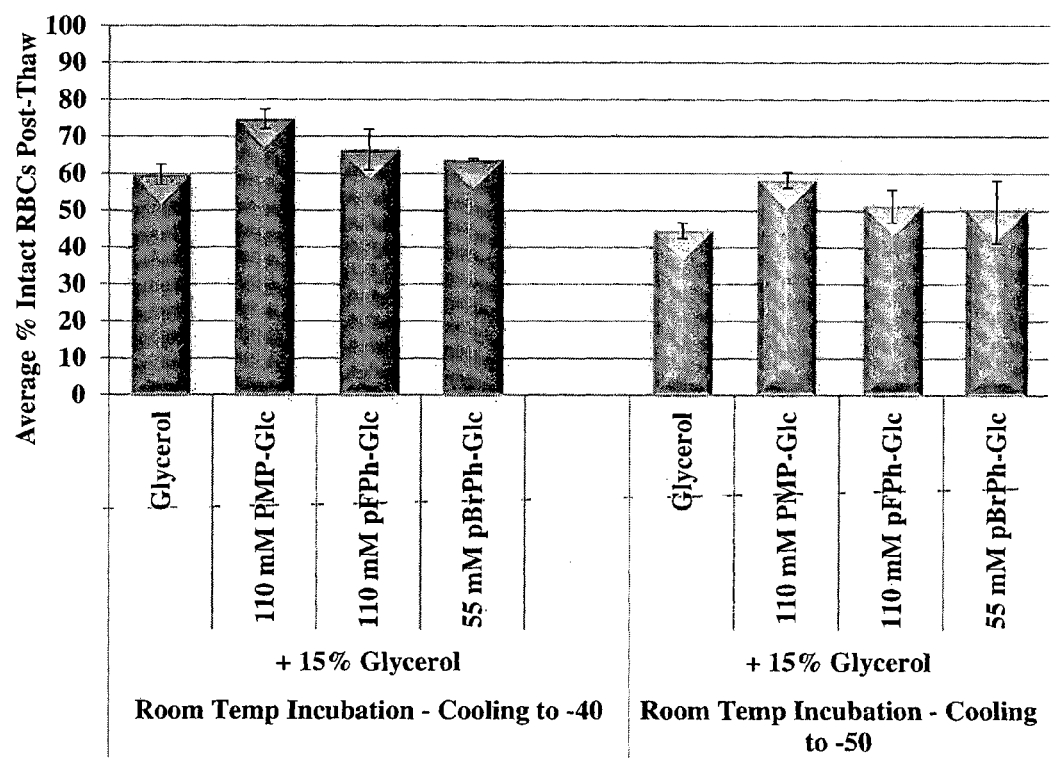
FIG. 22 is a graphical representation showing % intact (100-% hemolysis) for cryoprotectant solutions PMP-Glc (compound 17), pFPh-Glc (Compound 16), pBrPh-Glc (compound 14) and glycerol as well as glycerol alone used to preserve RBCs post-thaw during incubation with the cryoprotectant solution at room temperature and slow cooling to −40° C. and −50° C.
Figure 23:
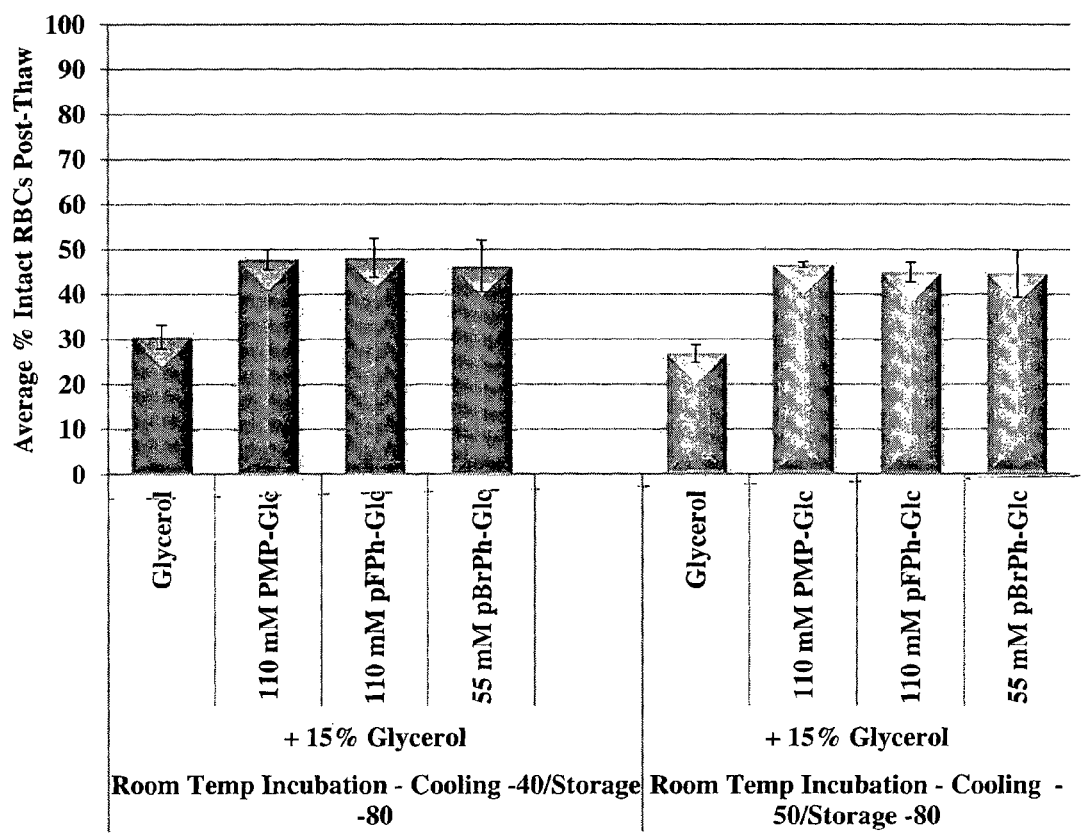
FIG. 23 is a graphical representation showing % intact (100-% hemolysis) for cryoprotectant solutions PMP-Glc (compound 17), pFPh (Compound 16), pBrPh-Glu (compound 14) and glycerol as well as glycerol alone used to preserve RBCs post-thaw during incubation with the cryoprotectant solution at room temperature and slow cooling to −40° C. and −50° C., and storage at −80° C. for 2 hours.

In the experiments summarized in FIGS. 22 and 23, two separate cryovials containing the RBCs were suspended in the cryoprotectant solution and placed in a cryobath where the temperature was decreased at precisely 1° C./minute. At −5° C., each sample was nucleated to ensure ice formation and the temperature was decreased at −1° C./minute until the desired temp was reached (−5, −15, −40 or −50). At this temperature, one of the cryovials was removed and thawed rapidly in a bath set to 37° C. The other sample was placed in a −80° C. freezer and stored for 1 hour. The sample was then thawed rapidly.

Example 7

Cryopreservation of Tf1-α (or Tf1-a) Cells with (i) DMSO Alone and (ii) Aryl-Aldonamides (Compounds 1a, 2a and 3s) With and Without DMSO Tf1-α cells were cultured to a final concentration of 2-3×106 cells/mL. Three million cells were transferred into cryovials and media were removed by aspiration after centrifugation at 1000 rpm for five minutes. 100 μL of RPMI media (10% FBS) supplemented with the cryopreservative of interest was added to the cryovial and vortexed. The cryovials were cooled at a rate of −1° C./min for 24 hours to −80° C. before being transferred to a liquid nitrogen dewar for storage until analysis.

Viability/Apoptosis Analysis

Figure 26A:
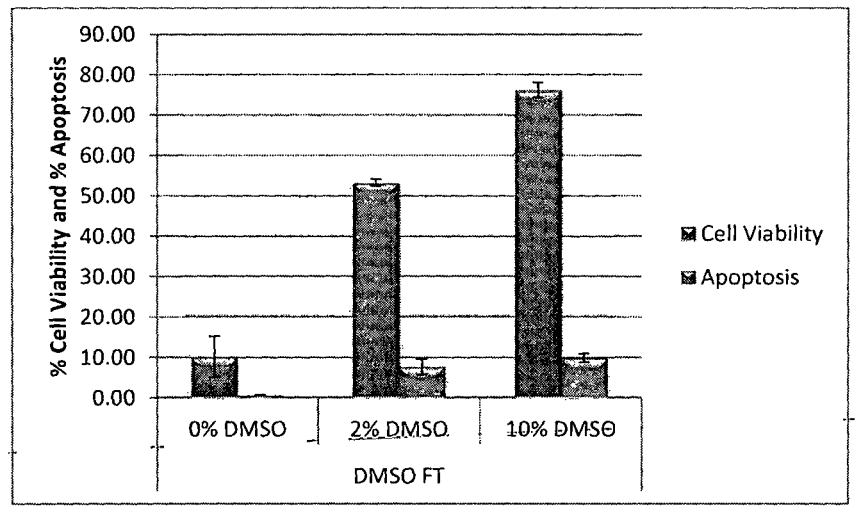
FIG. 26(a) is a graphical representation of Tf1-α (or Tf1-a) cell viability with 0%, 2% or 10% DMSO.

Cryovials were thawed under fast thaw conditions (submerged in 37° C. water bath). The cells were then diluted to a concentration of 3×10$^6$ cells/mL with 1× Annexin V Binding Buffer and a cell count was obtained by hemacytometer (to obtain cell recovery). A 400 μL aliquot was transferred to a flow cytometry tube. 10 μL of each Annexin V FITC (for apoptosis) and 7-AAD (for viability) dyes were added, the tube was vortexed and allowed to incubate in the dark for 15 minutes. The solution was diluted to 1 mL with 1× Annexin V Binding Buffer, vortexed and analyzed by flow cytometry. FIG. 26(a) shows the viability of the cells stored at −196° C. for 48 hours without a cryoprotectant solution, but only with 0%, 2% or 10% DMSO before flow cytometry analysis. With 2% DMSO, cell viability reached about 45%, and with 10% DMSO, cell viability reached around 78%.

Figure 26B:
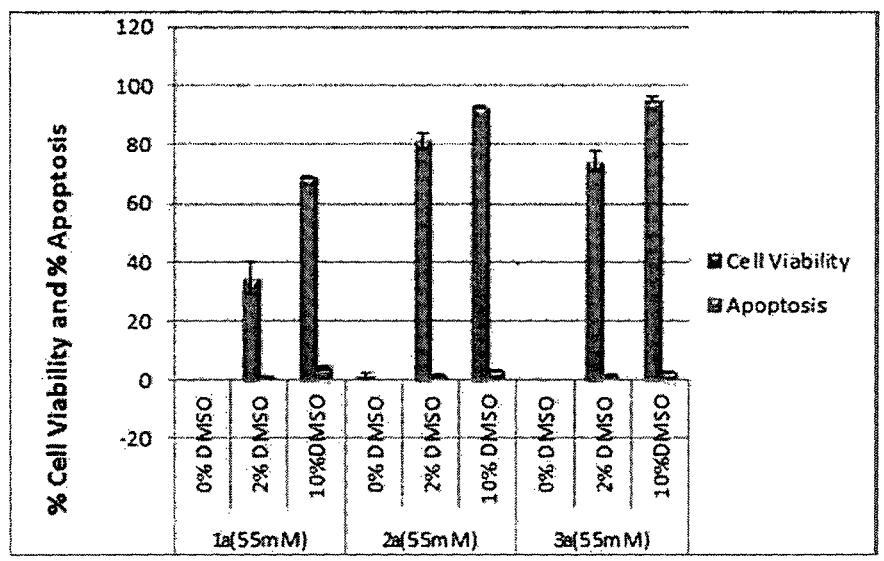
FIG. 26(b) is a graphical representation of Tf1-α cell viability for cryoprotectant solutions, each containing compounds 1a, 2a and 3a at 55 mM and 0%, 2% or 10% DMSO.

FIG. 26(b) shows Tf1-α cell viability when the cells were treated with a cryoprotectant solution containing an aryl-aldonamides of Formula B (compounds 1a, 2a and 3a) at 55 mM with 0%, 2% or 10% DMSO. The results are shown in Table 2.

TABLE 2

Cell viability and apoptosis of Tfl-α cells

| Aryl-aldonamides in the cryoprotectant solution (55 mM) | % DMSO | Cell Viability (%) | Apoptosis (%) |
|---|---|---|---|
| 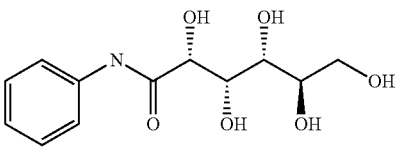 [SMILES: O=C(Nc1ccccc1)[C@H](O)[C@@H](O)[C@H](O)[C@H](O)CO] (1a) | 0<br>2<br>10 | 0.07<br>34.71<br>68.82 | 0<br>0.9<br>4.22 |
| 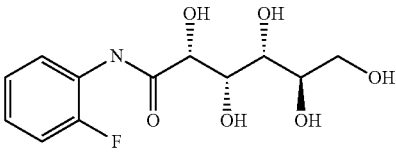 [SMILES: O=C(Nc1ccccc1F)[C@H](O)[C@@H](O)[C@H](O)[C@H](O)CO] (2a) | 0<br>2<br>10 | 1.27<br>81.28<br>92.83 | 0<br>1.5<br>3.37 |
| 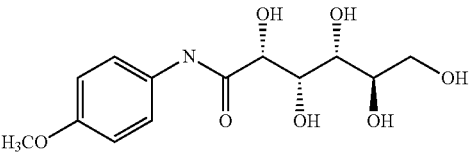 [SMILES: COc1ccc(NC(=O)[C@H](O)[C@@H](O)[C@H](O)[C@H](O)CO)cc1] (3a) | 0<br>2<br>10 | 0.16<br>74.33<br>95.33 | 0<br>1.38<br>2.73 |

What is claimed is:

1. A composition for cryopreserving a biological material comprising:
   at least one ice recrystallization inhibitor (IRI) compound selected from the group consisting of a n-alkyl-erythronamide, an aryl-glycoside, an aryl-aldonamide, and a combination thereof; and
   at least one cryopreservation agent.

2. The composition of claim 1, wherein the at least one IRI compound is an aryl-glycoside, an aryl-aldonamide or a combination thereof.

3. The composition of claim 1, wherein the at least one IRI compound is a para-, ortho- or meta-substituted aryl-glycoside.

4. The composition of claim 3, wherein the para-, ortho- or meta-substituted aryl-glycoside is a para-, ortho- or meta-substituted aryl-glucoside corresponding in structure to Formula A:

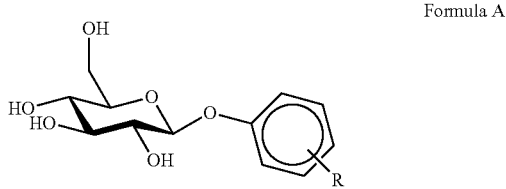

Formula A wherein R is hydrogen, halo, alkoxy, haloalkyl, alkyl or —NO$_2$.

5. The composition of claim 4, wherein R is hydrogen; or halo selected from the group consisting of Br, Cl, and F; or $C_1$-$C_4$-alkoxy; or $C_1$-$C_4$-haloalkyl; or $C_1$-$C_4$-alkyl; or —NO$_2$.

6. The composition of claim 4, wherein R is hydrogen; or halo selected from the group consisting of Br, Cl, and F; or $C_1$-$C_4$-alkoxy and wherein R is para-substituted.

7. The composition of claim 4, wherein the para-, ortho- or meta-substituted aryl-glucoside corresponding in structure to Formula A is para-methoxy-phenyl glucoside, para-fluoro-phenyl glucoside or para-bromo-phenyl glucoside.

8. The composition of claim 1, wherein the at least one IRI compound is an aryl-aldonamide.

9. The composition of claim 8, wherein the aryl-aldonamide is a phenyl-aldonamide corresponding in structure to Formula B:

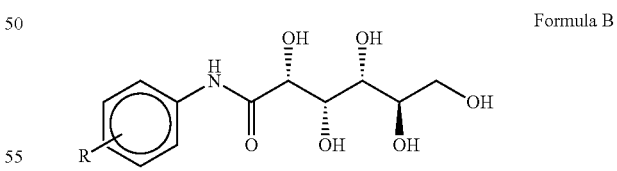

Formula B wherein R is hydrogen; $C_1$-$C_4$-alkoxy; or halo selected from the group consisting of Br, Cl, and F.

10. The composition of claim 9, wherein R is hydrogen; or R is a para-, ortho- or meta-substituted $C_1$-$C_4$-alkoxy; or R is an ortho-substituted halo selected from the group consisting of Br, Cl, and F.

11. The composition of claim 9, wherein the phenyl-aldonamide corresponding in structure to Formula B is

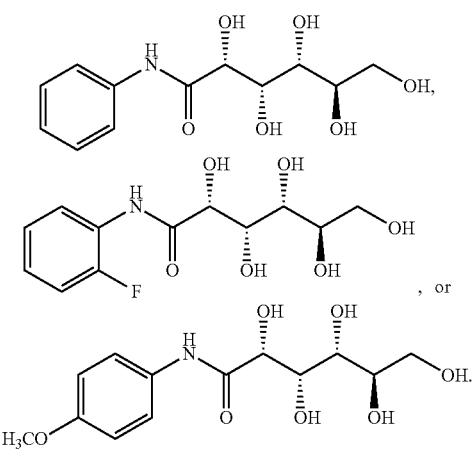

12. The composition of claim 1, wherein the at least one cryopreservation agent is selected from the group consisting of DMSO, glycerol, polyvinyl alcohol, and a combination thereof.

13. The composition of claim 1, wherein the at least one IRI compound is present in a concentration of about 55 mM to and including about 220 mM, and the at least one cryopreservation agent is present in a concentration of about 0.1% w/w to and including about 30% w/w.

14. The composition of claim 13, wherein the at least one cryopreservation agent is present in a concentration of about 0.1% w/w to and including about 20% w/w.

15. The composition of claim 1, further comprising a biological material selected from the group consisting of an organ, a tissue, and a cell.

16. The composition of claim 15, wherein the cell is selected from the group consisting of a cell line, a stem cell, a progenitor cell, a liver cell and a red blood cell.

17. The composition of claim 16, wherein the cell is a red blood cell, a progenitor cell, or a human liver cell.

18. The composition of claim 1, further comprising a cell medium.

19. The composition of claim 18, wherein the cell medium is selected from the group consisting of Eagle's minimum essential medium, Dulbecco's modified Eagle's medium, RPMI, fetal bovine serum, fetal calf serum, Ham's F-10, Ham's F-12, Medium 199, Hank's Buffered Salt Solution, Hank's Buffered Salt Solution and dextrose, and a combination thereof.

20. A kit for cryopreserving a biological material comprising the composition of any one of claim 1.

21. The kit of claim 20, further comprising a cell medium.

22. The kit of claim 21, wherein the cell medium is selected from the group consisting of Eagle's minimum essential medium, Dulbecco's modified Eagle's medium, RPMI, fetal bovine serum, fetal calf serum, Ham's F-10, Ham's F-12, Medium 199, Hank's buffered salt solution, Hank's Buffered Salt Solution and dextrose, and a combination thereof.

23. A method for cryopreserving a biological material comprising:
suspending the biological material in a solution comprising at least one IRI compound to form a suspension; and
freezing the suspension;
wherein the at least one IRI compound is selected from the group consisting of a n-alkyl-erythronamide, an aryl-glycoside, an aryl-aldonamide, and a combination thereof.

24. The method of claim 23, wherein the at least one IRI compound is an aryl-glycoside, an aryl-aldonamide or a combination thereof.

25. The method of claim 23, wherein the at least one IRI compound is a para-, ortho- or meta-substituted aryl-glycoside.

26. The method of claim 25, wherein the para-, ortho- or meta-substituted aryl-glycoside is present in the solution in a concentration between about 55 nM and about 110 mM inclusive.

27. The method of claim 25, wherein the para-, ortho- or meta-substituted aryl-glycoside is a para, ortho- or meta-substituted aryl-glucoside corresponding in structure to Formula A:

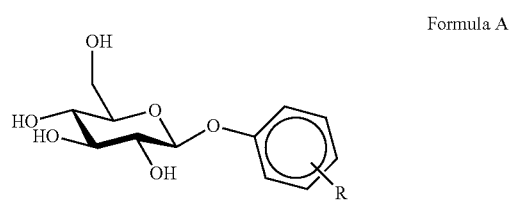

Formula A wherein R is hydrogen, halo, alkoxy, haloalkyl, alkyl or —$NO_2$.

28. The method of claim 27, wherein R is hydrogen; or halo selected from the group consisting of Br, Cl, and F; or $C_1$-$C_4$-alkoxy; or $C_1$-$C_4$-haloalkyl; or $C_1$-$C_4$-alkyl; or —$NO_2$.

29. The method of claim 27, wherein R is hydrogen; or halo selected from the group consisting of Br, Cl, and F; or $C_1$-$C_4$-alkoxy and wherein R is para-substituted.

30. The method of claim 29, wherein the para-, ortho- or meta-substituted aryl-glucoside corresponding in structure to Formula A is para-methoxy-phenyl glucoside, para-fluoro-phenyl glucoside or para-bromo-phenyl glucoside.

31. The method of claim 23, wherein the at least one IRI compound is an aryl-aldonamide.

32. The method of claim 31, wherein the aryl-aldonamide is a phenyl-aldonamide corresponding in structure to Formula B:

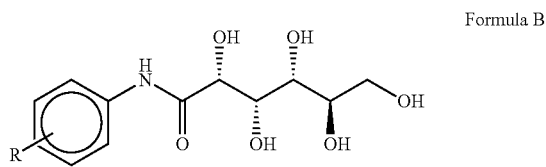

Formula B wherein R is hydrogen; $C_1$-$C_4$-alkoxy; or halo selected from the group consisting of Br, Cl, and F.

33. The method of claim 32, wherein R is hydrogen; or R is a para-, ortho- or meta-substituted $C_1$-$C_4$-alkoxy; or R is an ortho-substituted halo selected from the group consisting of Br, Cl, and F.

34. The method of claim 32, wherein the phenyl-aldonamide corresponding in structure to Formula B is

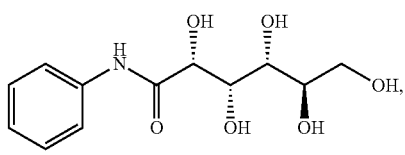

-continued

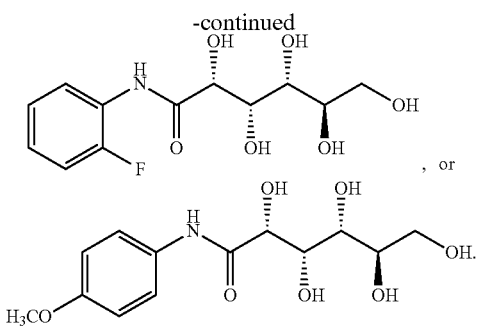

, or

35. The method of claim 23, wherein the at least one IRI compound is present in the solution in a positive concentration of less than about 400 mM.

36. The method of claim 35, wherein the at least one IRI compound is present in the solution in a concentration of less than about 10 mM.

37. The method of claim 23, wherein the biological material is selected from the group consisting of an organ, a tissue and a cell.

38. The method of claim 37, wherein the cell is selected from the group consisting of a cell line, a stem cell, a progenitor cell, a liver cell and a red blood cell.

39. The method of claim 38, wherein the biological material comprises a red blood cell, a progenitor cell or a liver cell.

40. The method of claim 23, wherein freezing the suspension comprises performing rate controlled freezing of about 1° C. per minute over about 16 hours.

41. The method of claim 23, wherein freezing the suspension comprises freezing the suspension directly into a storage unit without performing rate controlled freezing.

42. The method of claim 23, wherein freezing the suspension is performed in liquid nitrogen to about −196° C. or in dry ice to about −80° C.

43. The method of claim 23, wherein the solution of at least one IRI compound further comprises at least one cryopreservation agent.

44. The method of 43, wherein the at least one cryopreservation agent comprises DMSO, glycerol, polyvinyl alcohol or a combination thereof.

45. The method of claim 43, wherein the least one cryopreservation agent is present in the solution in a positive amount of about 30% or less of the total solution.

46. The method of claim 45, wherein the least one cryopreservation agent is present in the solution in a positive amount of about 20% or less of the total solution.

47. The method of claim 23, wherein the solution comprising the at least one IRI compound further comprises a cell medium.

48. The method of claim 47, wherein the cell medium is selected from the group consisting of Eagle's minimum essential medium, Dulbecco's modified Eagle's medium, RPMI, fetal bovine serum, fetal calf serum, Ham's F-10, Ham's F-12, Medium 199, Hank's buffered salt solution, HBSS and dextrose, and a combination thereof.

* * * * *